US009826400B2

(12) United States Patent
Jakobsson

(10) Patent No.: US 9,826,400 B2
(45) Date of Patent: Nov. 21, 2017

(54) METHOD AND APPARATUS THAT FACILITATES A WEARABLE IDENTITY MANAGER

(71) Applicant: QUALCOMM Incorporated, San Diego, CA (US)

(72) Inventor: Bjorn Markus Jakobsson, Portola Valey, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 14/444,620

(22) Filed: Jul. 28, 2014

(65) Prior Publication Data

US 2015/0286813 A1   Oct. 8, 2015

Related U.S. Application Data

(60) Provisional application No. 61/975,684, filed on Apr. 4, 2014.

(51) Int. Cl.
*G06F 21/00* (2013.01)
*H04W 12/06* (2009.01)
(Continued)

(52) U.S. Cl.
CPC ............. *H04W 12/06* (2013.01); *A61B 5/681* (2013.01); *G06F 1/163* (2013.01); *G06F 3/0346* (2013.01);
(Continued)

(58) Field of Classification Search
CPC .......... G06F 21/35; G06F 21/32; G06F 21/34; G06F 1/163; G06F 3/0346;
(Continued)

(56) References Cited

U.S. PATENT DOCUMENTS 6,695,207 B1 *   2/2004   Norris, Jr. ............... B60R 25/23
                                                235/380
6,757,719 B1 *   6/2004   Lightman ............ G06Q 20/383
                                                455/419
(Continued)

FOREIGN PATENT DOCUMENTS

WO     WO-2013079609 A1     6/2013

OTHER PUBLICATIONS

International Search Report and Written Opinion—PCT/US2015/023719—ISAEPO—dated Jun. 16, 2015.
(Continued)

*Primary Examiner* — Sarah Su
(74) *Attorney, Agent, or Firm* — Loza & Loza, LLP

(57) ABSTRACT

Various aspects directed towards a wearable identity manager system are disclosed. In a first aspect, an association status between a user and a wearable identity manager device is ascertained based on whether the wearable identity manager device is worn by the user, and motion data associated with a movement of the wearable identity manager device is monitored. Authentication data, which includes the motion data, is then transmitted based on the association status. In another aspect, an association status between a user and a wearable identity manager device is again determined based on whether the wearable identity manager device is worn by the user. Here, however, the wearable identity manager device is paired with a pairing device, and authentication data is transmitted to the pairing device based on the association status to facilitate a user authentication via the pairing device.

30 Claims, 19 Drawing Sheets

(51) Int. Cl.

| | |
|---|---|
| *G06F 21/35* | (2013.01) |
| *H04L 29/06* | (2006.01) |
| *A61B 5/00* | (2006.01) |
| *G06F 1/16* | (2006.01) |
| *G06F 21/32* | (2013.01) |
| *G06F 3/0346* | (2013.01) |
| *G06F 21/34* | (2013.01) |
| *A61B 5/024* | (2006.01) |
| *A61B 5/11* | (2006.01) |

(52) U.S. Cl.
CPC .............. *G06F 21/32* (2013.01); *G06F 21/34* (2013.01); *G06F 21/35* (2013.01); *H04L 63/0853* (2013.01); *A61B 5/02438* (2013.01); *A61B 5/1116* (2013.01); *A61B 5/6844* (2013.01)

(58) Field of Classification Search
CPC .... H04L 63/0853; H04W 12/06; A61B 5/681; A61B 5/02438; A61B 5/1116; A61B 5/6844
USPC ...... 726/2, 3, 4, 9, 16, 17, 20; 713/182, 185
See application file for complete search history.

(56) References Cited

U.S. PATENT DOCUMENTS

| | | | |
|---|---|---|---|
| 8,112,066 B2 | 2/2012 | Ben | |
| 8,181,881 B2 | 5/2012 | Pedicano | |
| 8,430,310 B1* | 4/2013 | Ho | G06F 21/35 235/382 |
| 9,185,100 B1* | 11/2015 | Juels | H04W 4/023 |
| 2002/0175990 A1* | 11/2002 | Martino | H04N 7/142 348/14.08 |
| 2003/0025603 A1* | 2/2003 | Smith | G06F 21/35 340/572.8 |
| 2006/0281409 A1 | 12/2006 | Levien et al. | |
| 2007/0003061 A1 | 1/2007 | Jung et al. | |
| 2008/0238667 A1* | 10/2008 | Olson | G06K 19/0723 340/541 |
| 2010/0052916 A1 | 3/2010 | Canora et al. | |
| 2010/0075631 A1* | 3/2010 | Black | H04M 1/05 455/410 |
| 2011/0248853 A1 | 10/2011 | Roper et al. | |
| 2012/0122435 A1* | 5/2012 | Sarkissian | H04M 1/6066 455/414.1 |
| 2012/0317024 A1* | 12/2012 | Rahman | G06Q 30/02 705/42 |
| 2013/0094866 A1 | 4/2013 | Pasquero et al. | |
| 2013/0173658 A1 | 7/2013 | Adelman et al. | |
| 2014/0071041 A1* | 3/2014 | Fujimaki | G02B 27/0172 345/156 |
| 2014/0082707 A1* | 3/2014 | Egan | H04L 63/0853 726/5 |
| 2014/0089672 A1* | 3/2014 | Luna et al. | 713/186 |
| 2014/0106677 A1 | 4/2014 | Altman | |
| 2014/0139422 A1* | 5/2014 | Mistry | G06F 3/014 345/156 |
| 2014/0249853 A1 | 9/2014 | Proud et al. | |
| 2014/0282878 A1* | 9/2014 | Ignatchenko | H04L 63/08 726/3 |
| 2014/0316792 A1 | 10/2014 | Siddiqui | |
| 2014/0325220 A1* | 10/2014 | Tunnell | G06F 21/00 713/168 |
| 2014/0335789 A1 | 11/2014 | Cohen et al. | |
| 2014/0337634 A1* | 11/2014 | Starner | H04L 9/3231 713/186 |
| 2014/0358794 A1* | 12/2014 | Finley | G06Q 20/382 705/71 |
| 2014/0359744 A1* | 12/2014 | Hillis | H04L 63/0853 726/9 |
| 2015/0035644 A1* | 2/2015 | June | G07C 11/00 340/5.61 |
| 2015/0040203 A1* | 2/2015 | Qian | G06F 21/32 726/7 |
| 2015/0061842 A1* | 3/2015 | Yoon | G04G 21/04 340/12.5 |
| 2015/0088007 A1* | 3/2015 | Bardy | A61B 5/0022 600/484 |
| 2015/0135259 A1* | 5/2015 | Ilyadis | H04L 63/0227 726/1 |
| 2015/0163221 A1* | 6/2015 | Bolin | G07C 9/00309 726/7 |
| 2015/0186636 A1* | 7/2015 | Tharappel | G06F 21/32 726/8 |
| 2015/0193785 A1* | 7/2015 | Besehanic | G06Q 30/0201 705/7.32 |
| 2015/0206413 A1* | 7/2015 | Warner | G06Q 50/22 340/573.1 |
| 2015/0278498 A1* | 10/2015 | Hong | G06F 21/32 340/5.82 |
| 2015/0332031 A1* | 11/2015 | Mistry | G06F 21/316 726/19 |
| 2015/0350362 A1* | 12/2015 | Pollack | H04L 67/2861 709/217 |
| 2015/0372746 A1* | 12/2015 | Xie | H04B 7/155 455/11.1 |
| 2015/0381602 A1* | 12/2015 | Grim | H04L 63/08 726/4 |
| 2015/0382195 A1* | 12/2015 | Grim | H04L 63/08 726/4 |
| 2016/0066178 A1* | 3/2016 | Hawkins | H04W 8/265 455/435.1 |
| 2016/0080941 A1 | 3/2016 | Jakobsson | |
| 2016/0088474 A1 | 3/2016 | Smith et al. | |
| 2016/0135046 A1* | 5/2016 | Archibald | H04W 12/06 455/411 |
| 2016/0250490 A1 | 9/2016 | Hoffman et al. | |
| 2016/0338640 A1* | 11/2016 | Chan | A61B 5/4884 |
| 2016/0379205 A1* | 12/2016 | Margadoudakis | G06Q 20/327 705/71 |
| 2017/0095153 A1* | 4/2017 | Bardy | A61B 5/0006 |
| 2017/0150305 A1* | 5/2017 | Chaudhri | H04W 4/02 |

OTHER PUBLICATIONS

Kobsa A., et al., "Serial Hook-Ups: A Comparative Usability Study of Secure Device Pairing Methods," Proceedings of the 5th Symposium on Usable Privacy and Security (SOUPS), Jan. 1, 2009, p. 1, XP055194285.

Mayrhofer R., et al., "Shake Well Before Use: Authentication Based on Accelerometer Data," Pervasive Computing, Lecture Notes in Computer Science, May 13, 2007, vol. 4480, pp. 144-161, XP019079249.

\* cited by examiner

METHOD AND APPARATUS THAT FACILITATES A WEARABLE IDENTITY MANAGER

CROSS-REFERENCE TO RELATED APPLICATIONS

This application claims priority to and the benefit of U.S. Provisional Patent Application No. 61/975,684, filed on Apr. 4, 2014, the entire content of which is hereby incorporated by reference.

BACKGROUND

Field

Aspects of the present disclosure relate generally to wireless communication systems, and more particularly, to a wearable identity manager system that facilitates authenticating a user.

Background

User authentication is an increasing source of frustration and fraud risk. Typical consumers use the same or very similar password for multiple services, which increases exposure to fraud that breaches cause. Many users resist using services requiring passwords on mobile devices, due to the difficulties of entering passwords. While password managers can be used, they increase the exposure to friendly fraud (i.e., abusive transactions initiated by users close to the device owner) and increase the risks associated with device loss. Similarly, personal identification numbers (PINs) and other forms of memory-based authentication pose similar problems.

SUMMARY

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

Aspects of the present disclosure provide methods, apparatuses, computer program products, and processing systems directed towards a wearable identity manager system that facilitates authenticating a user. In one aspect, the disclosure provides a method to facilitate transactions, which includes determining an association status between a user and a wearable identity manager device based on whether the wearable identity manager device is worn. The method further includes pairing the wearable identity manager device with a pairing device, and transmitting authentication data to the pairing device based on the association status to facilitate a user authentication via the pairing device.

In another aspect, a wearable identity manager device configured to facilitate transactions is disclosed. The wearable identity manager comprises a detector component, a determining component, and a transmitting component. Here, the detector component is configured to determine an association status between a user and the wearable identity manager device based on whether the wearable identity manager device is worn, whereas the determining component is configured to facilitate determining a user authentication via a sensor component configured to monitor motion data associated with a movement of the wearable identity manager device. The transmitting component is then configured to transmit authentication data based on the association status, such that the authentication data includes the motion data.

In a further aspect, another wearable identity manager device configured to facilitate transactions is disclosed. Here, the device comprises means for determining an association status between a user and the wearable identity manager device based on whether the wearable identity manager device is worn, and means for pairing the wearable identity manager device with a pairing device. The wearable identity manager device further comprises means for transmitting authentication data to the pairing device based on the association status, such that the authentication data facilitates a user authentication via the pairing device.

In yet another aspect, a non-transitory machine-readable storage medium configured to facilitate transactions via one or more instructions stored thereon is disclosed. Here, when executed by at least one processor, the one or more instructions cause the at least one processor to perform various acts. The acts include ascertaining an association status between a user and a wearable identity manager device based on whether the wearable identity manager device is worn, and monitoring motion data associated with a movement of the wearable identity manager device. The acts further include transmitting authentication data based on the association status, such that the authentication data includes the motion data.

These and other disclosed aspects will become more fully understood upon a review of the detailed description, which follows. Other aspects, features, and aspects of the present invention will become apparent to those of ordinary skill in the art, upon reviewing the following description of specific, exemplary aspects of the present invention in conjunction with the accompanying figures. While features of the present invention may be discussed relative to certain aspects and figures below, all aspects of the present invention can include one or more of the advantageous features discussed herein. In other words, while one or more aspects may be discussed as having certain advantageous features, one or more of such features may also be used in accordance with the various aspects of the invention discussed herein. In similar fashion, while exemplary aspects may be discussed below as device, system, or method aspects it should be understood that such exemplary aspects can be implemented in various devices, systems, and methods.

DETAILED DESCRIPTION

Overview

As discussed in the background, because of the various limitations of conventional user authentication mechanisms, users often undesirably refrain from wireless-based authentication transactions so as to shield themselves from potential fraud. The aspects disclosed herein are directed towards overcoming such limitations by providing an authentication infrastructure that authenticates users based on whether they are wearing a wearable identity manager device. Namely, aspects are disclosed which enable users to associate themselves with a wearable identity manager device, wherein the wearable identity manager device is configured to facilitate a wireless authentication of the user to another device so long as the wearable identity manager device is continuously worn by the user.

Exemplary Wearable Identity Manager Device

Figure 1:
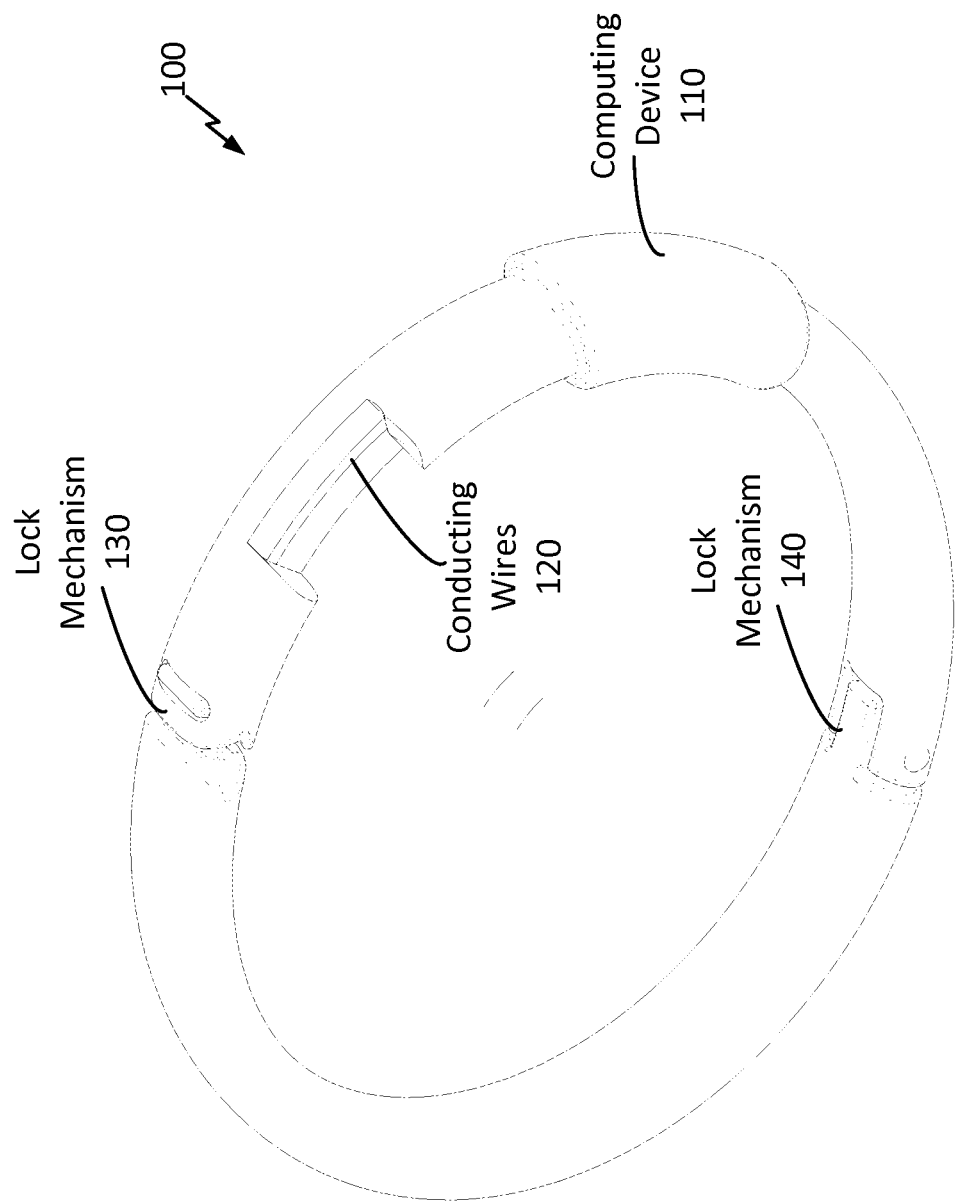
FIG. 1 is a schematic of an exemplary wearable identity manager device in accordance with an aspect of the disclosure.
Figure 2:
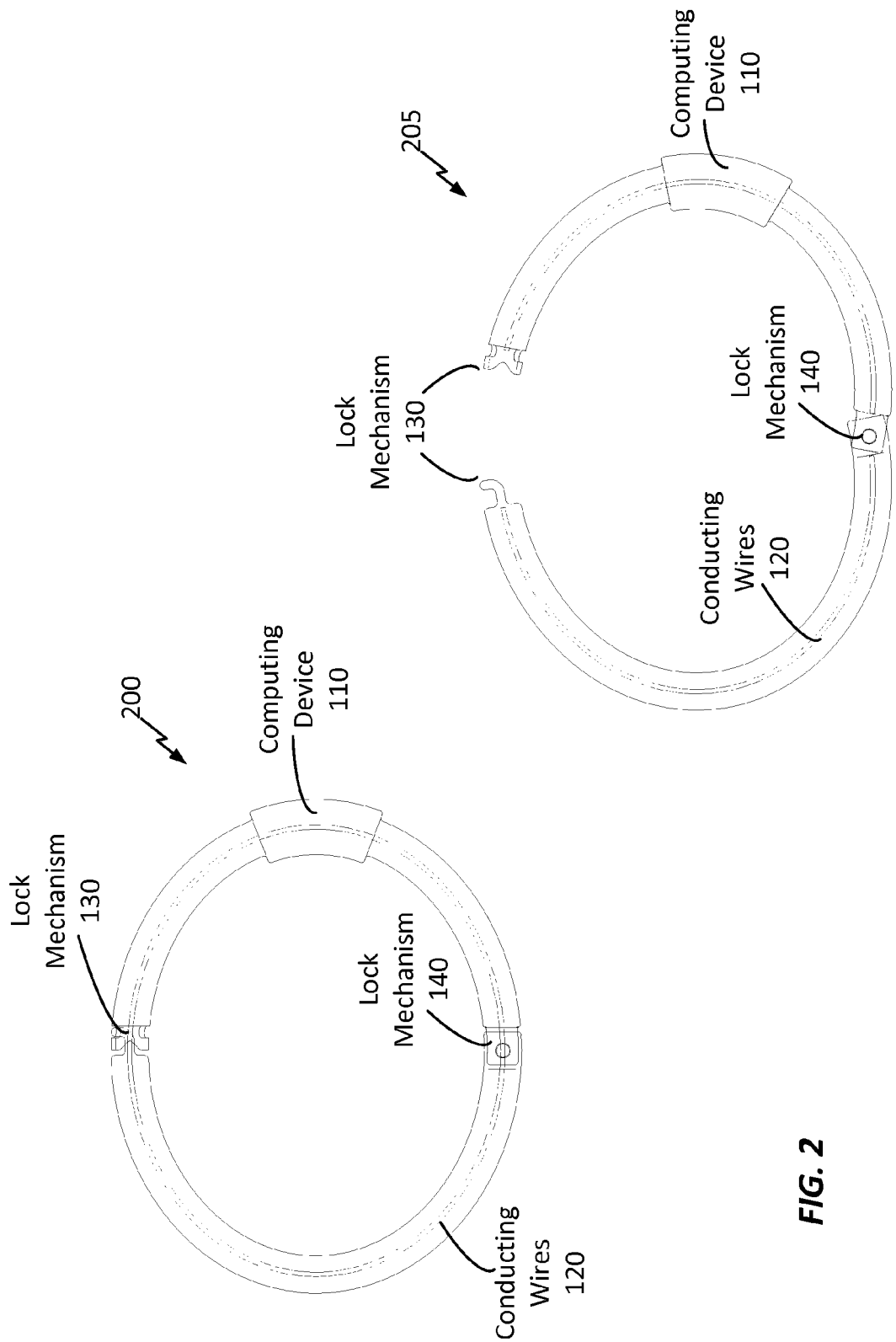
FIG. 2 is a schematic illustrating an exemplary wearable identity manager device in a locked and unlocked configuration.

Referring next to FIG. 1, an exemplary wearable identity manager device is provided in accordance with an aspect of the disclosure. As illustrated, wearable identity manager device 100 is configured as a wearable bracelet comprising a first lock mechanism 130 and a second lock mechanism 140. Wearable identity manager device 100 also comprises computing device 110 and conducting wires 120, wherein computing device 110 is configured to detect whether a connection between conducting wires 120 is broken. Namely, as illustrated in FIG. 2, it is contemplated that wearable identity manager device 100 is attachable to a user via lock mechanism 130, wherein a locked configuration 200 creates a closed circuit between conducting wires 120, and wherein an unlocked configuration 205 breaks the circuit between conducting wires 120. Moreover, it is contemplated that computing device 110 will detect whether wearable identity manager device 100 is worn by a user according to whether a connection between conducting wires 120 is broken (i.e., unlocked configuration 205) or closed (i.e., locked configuration 200).

As will be discussed in more detail below, enabling wearable identity manager device 100 to facilitate an authentication of a user to other devices may first require an association between wearable identity manager device 100 and the user. For instance, upon attaching wearable identity manager device 100 to his/her wrist, a user may be required to enter a password (e.g., via a user interface on computing device 110 or via another device paired to wearable identity manager device 100) so as to confirm the user's identity to wearable identity manager device 100. Upon confirming the user's identity, it is contemplated that wearable identity manager device 100 could then facilitate subsequent user authentications with other entities (e.g., point-of-sale devices, toll booths, financial institution websites, etc.) by wirelessly transmitting authentication data to those entities, so long as lock mechanism 130 remains in a locked configuration. Otherwise, if computing device 110 detects that lock mechanism 130 has become unlocked, computing device 110 will infer that the user is no longer wearing wearable identity manager device 100, and will thus not transmit authentication data until the user re-associates with wearable identity manager device 100.

In alternative implementations, rather than using a locking mechanism, any of various other devices may be used to detect whether wearable identity manager device 100 is worn by a user. For instance, wearable identity manager device may further comprise a pulse sensor. Here, if the pulse sensor has not detected a signal for a predetermined amount of time (e.g., thirty seconds), then wearable identity manager device 100 may infer that the user is no longer wearing the device. As soon as a pulse is detected again, wearable identity manager device 100 may infer that it is likely being worn, which causes it to re-enter an identity acquisition mode. If there is no communication detected for some portion of time, such as one minute, after identity acquisition mode has been initiated, the device may return to disassociated mode, or may send a signal to wake up devices used as proxies in the identity acquisition mode.

An accelerometer sensor can also be used to determine whether wearable identity manager device 100 is worn. Within such implementation, if no signal is detected by the accelerometer, or only movements that are not indicative of the device being worn, for at least a threshold amount of time (e.g., five minutes), then wearable identity manager device 100 would become disassociated, meaning that it would no longer represent the user it previously represented. When a sufficiently strong accelerometer signal is again detected, wearable identity manager device 100 would place itself into identity acquisition mode for some amount of time, or until an identity has been acquired. Other functionally related sensors, such as gyros, can also be used, whether in combination with an accelerometer, or as an alternative to it.

Yet another sensor that can be used to determine whether wearable identity manager device 100 is worn is a pressure or touch sensor. Such a sensor may be particularly desirable for users who wear wearable identity manager device 100 tightly to their body (e.g., a tight fitting bracelet, ring, etc.). If there is no pressure/touch detected for some amount of time, then wearable identity manager device 100 disassociates itself from the identity it previously represented. When pressure/touch is again detected, wearable identity manager device 100 returns to identity acquisition mode.

A stretch sensor implementation is also contemplated. For instance, if wearable identity manager device 100 is configured as a stretchable bracelet, it is contemplated that wearable identity manager device 100 will be stretched upon removal from the user. Accordingly, wearable identity manager device 100 may comprise a stretch sensor configured to detect whether wearable identity manager device 100 has been stretched beyond a threshold stretch metric. Within such implementation, wearable identity manager device 100 may then be configured to trigger an association/disassociation process based on data received from the stretch sensor.

Sensors can also be included to detect an explicit user action indicating a user's desire to associate/disassociate. Here, an explicit action to disassociate might be more deliberate than an explicit action to associate, so as to protect against inadvertent disassociations. For example, a gyro sensor may be included to detect rapid spinning, of a kind users cannot typically engage in while wearing wearable identity manager device 100, which would cause disassociation. The same or another movement can be used to identify the need to associate.

Wearable identity manager device 100 may also include a button configured to signal the desire to change state. For example, by pressing such button for ten seconds, wearable identity manager device 100 might be configured to disassociate, whereas pressing the same button three times in a row might cause wearable identity manager device 100 to attempt to acquire an identity.

It is also contemplated that explicit user actions can be combined with implicit user actions. For example, if a button is pressed for ten seconds while wearable identity manager device 100 is deemed to be stationary for at least a minute (e.g., via accelerometer data), then a disassociation might be performed. Identity acquisition may then be initiated if wearable identity manager device 100 is spun or rapidly shaken, while a pulse sensor detects a heartbeat.

For this particular example, although wearable identity manager device 100 is configured as a bracelet, it should be appreciated that any of various wearable configurations are contemplated. For instance, a necklace-shaped configuration is also contemplated, wherein such configuration has two parts: a string-component and a lock component. Here, the user knows that when he/she puts the necklace on and closes the lock, it is possible to enter the association mode in which an identity is selected and made available for consecutive authentication sessions with other entities. Similarly, the user knows that when she opens the lock, it is no longer possible to use the necklace for authentication without first going through another association session.

In a further example, the wearable identity manager device 100 is configured as a belt. If the user closes the buckle, then the wearable identity manager device 100 is set to identity acquisition mode. Moreover, if an accelerometer associated with the belt detects no movement for a minute, then the wearable identity manager device 100 enters an identity disassociation mode. In a particular aspect of the disclosure, the wearable identity manager device 100 is contemplated to operate as a master device in conjunction with a slave device. For instance, wearable identity manager device 100 may be a belt device configured to determine whether the belt is worn, and further configured to maintain an identity so long as the belt continues to be worn. A slave device (e.g., a ring, smart watch, bracelet, etc.) may then be utilized to determine intent, wherein the slave device may communicate with the master device via any of various communication protocols (e.g., Bluetooth LE). Here, such intent may be validated by requiring a user to perform an explicit action on the slave device while the master device is worn, and thus associated with the user. For instance, intent may be validated by pressing a button on the slave device while the master device is worn. Upon receiving an indication from the slave device that the button validation has indeed been executed, the master device may then further authenticate the transaction based on any of various factors. For instance, metadata received from the slave device and associated with the button validation (e.g., when the button was pressed, location data of the slave device, motion data of the slave device, etc.) can be synchronized or otherwise compared with master device data (e.g., location data of the master device, motion data of the master device, etc.) to authenticate the user.

In general, it should thus be appreciated that wearable identity manager device 100 can be configured as any of various stand-alone wearable items, such as bracelets, smart watches, rings, tattoos, belts, clothing, etc., which include electronic circuits. Wearable identity manager device 100 can also be configured as a button-sized battery, for example, and used instead of conventional batteries. Wearable identity manager device 100 can also be configured as printable stickers and placed on any of various wearable items, such as the back of watches, the charm on a necklace, etc. For stickers and patches, the identity acquisition may begin as the backing is removed, whereas the disassociation may begin once the circuit is damaged from the sticker or patch being torn off.

In an aspect of the disclosure, various protections against potential thieves can be readily implemented. For instance, once the disclosed technology becomes widely known, would-be thieves will know that if they were to steal a person's bag, containing a phone or other portable device, and this person uses a wearable identity manager device for authentication, then the device will be locked. This protects against the undesirable use of the wearable identity manager device by people who may borrow or steal a wearable identity manager device that is taken off.

In another exemplary scenario, it is desirable for would-be thieves to know that tearing the necklace-shaped wearable identity manager device from a victim's neck will automatically disassociate the wearable identity manager from the user and his/her account, since the circuit will be broken as the necklace is torn. This will have the same effect as taking off the necklace. As stated previously, this may be achieved by embedding a conductible wire throughout the necklace, including the lock. Alternatively, however, a second circuit is embedded in the necklace, running from the processor to the lock, and then back; and then to the other part of the lock, and back. If this second circuit is ever broken, that is not an indication that the necklace has been taken off, but that it has been torn off, which can be used to initiate an alert signal. The alert signal may be transmitted to a security company or police, and may be used to communicate a lock-down directive to any mobile device associated with the wearable identity manager device, thereby encrypting resources and alerting service providers. The resources may then only be accessible later, after a backup of the encryption key is obtained, as will be described in more detail below.

In yet another aspect, a kidnapping scenario is contemplated. Within such scenario, it would be desirable to configure the wearable identity manager device so that a sufficiently motivated person may physically remove the wearable identity manager device without disassociating it from the user. Indeed, such configuration may be particularly desirable for scenarios in which a kidnapper might consider harming the victim in order to avoid disassociating the wearable identity manager device upon removal. Referring back to FIG. 1, a possible solution to this problem is disclosed herein. Namely, a dual circuit design is contemplated, wherein a primary connection between conducting wires 120 is severable by unlocking locking mechanism 130, and wherein a secondary connection between conducting wires 120 is severable by unlocking locking mechanism 140. Here, by opening locking mechanism 140, a user can remove wearable identity manager device 100 without breaking the primary connection between conducing wires 120, which preserves the association between wearable identity manager device 100 and the user (thereby providing security against brutal attacks). In an aspect of the disclosure, locking mechanism 140 is significantly more difficult to open than locking mechanism 130. Alternatively, locking mechanism 140 can be designed to allow unlocking but not subsequent locking. Moreover, individual components of locking mechanism 140 may be mounted next to each other, so that they are in constant contact within one and the same physical lock. This way, the entire circuit can be contained in a traditional looking necklace, bracelet or watchband, avoiding two separate strands or two different locks.

Exemplary Wearable Identity Authentication System

Figure 3:
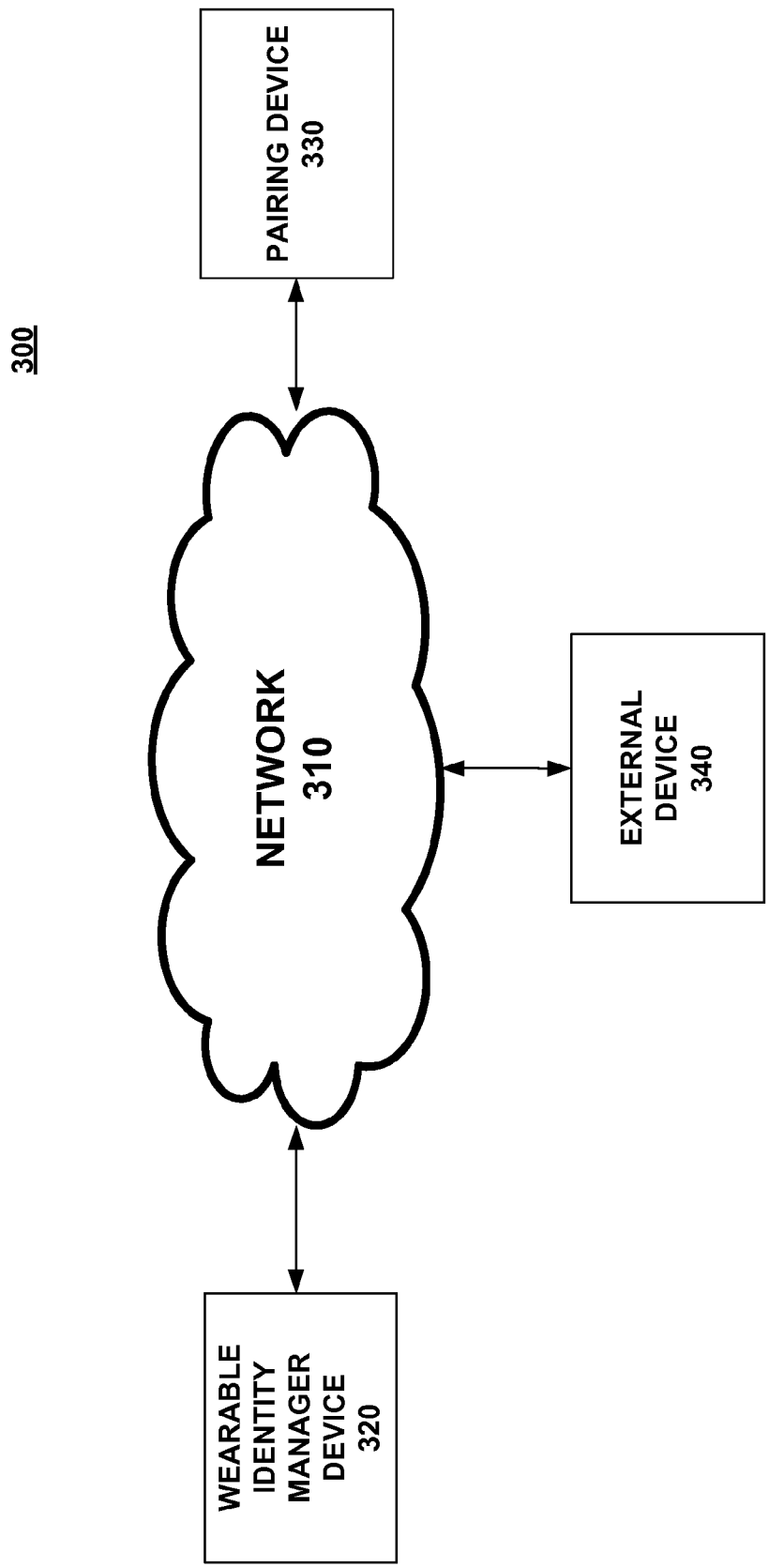
FIG. 3 illustrates an exemplary environment that facilitates authenticating a user via a wearable identity manager device in accordance with an aspect of the subject specification.

Turning now to FIG. 3, an exemplary environment that facilitates authenticating a user via a wearable identity manager device is provided according to an aspect of the disclosure. As illustrated, environment 300 includes wearable identity manager device 320, which may be coupled to pairing device 330 and external device 340 via network 310 (e.g., the Internet, peer-to-peer network, etc.). Here, it is contemplated that wearable identity manager device 320 may be configured as a radio-enabled device, wherein wearable identity manager device 320 is generally analogous to any of the wearable identity manager devices disclosed herein. For this particular example, assuming wearable identity manager device 320 is properly associated with a user and attached thereto, wearable identity manager device 320 may facilitate authenticating the user to an external device 340 corresponding to any of various types of entities (e.g., point-of-sale devices, toll booths, financial institution websites, etc.) by wirelessly transmitting authentication data to external device 340. Alternatively, rather than transmitting authentication data directly to external device 340, wearable identity manager device 320 may be configured to transmit such authentication data via pairing device 330 (e.g., a smartphone, personal computer, etc.), wherein such data may reside in wearable identity manager device 320 and/or pairing device 330, as discussed in more detail below.

Exemplary Wearable Identity Authentication Process

Figure 4:
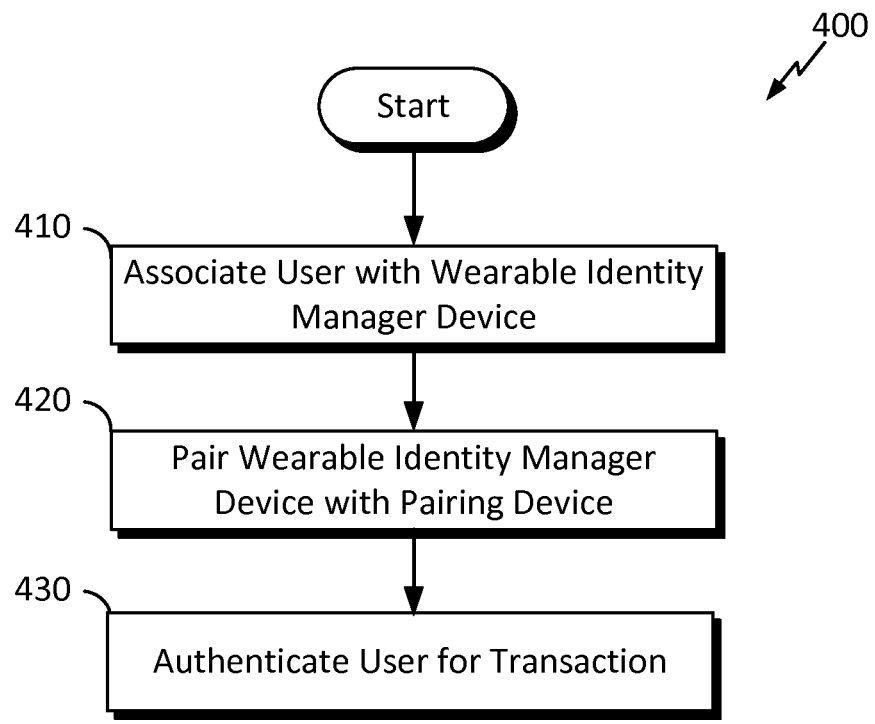
FIG. 4 is a flow chart illustrating an exemplary process to facilitate utilizing a wearable identity manager device according to some aspects of the disclosure.

Referring next to FIG. 4, a flow chart illustrating an exemplary process to facilitate utilizing a wearable identity manager device according to an aspect of the disclosure is provided. As illustrated, process 400 includes a series of acts that may be performed within any of various types of computing devices (e.g., wearable identity manager device 320, pairing device 330, and/or external entity 340) according to an aspect of the subject specification. For instance, process 400 may be implemented by employing a processor to execute computer executable instructions stored on a computer readable storage medium to implement the series of acts. In another aspect, a computer-readable storage medium comprising code for causing at least one computer to implement the acts of process 400 is contemplated.

As illustrated, process 400 begins at act 410 where a user is associated with a wearable identity management device so as to confirm the user's identity to the wearable identity manager device. Such association process may be initiated when the wearable identity management device is placed around the wrist of a user, around the neck of the user, or otherwise worn or physically associated with the user. Moreover, the wearable identity manager device detects a situation in which it is potentially becoming worn by a user, e.g., by a clasp, lock or buckle being closed. Conversely, a disassociation process commences when the wearable identity manager device is taken off (e.g., removing the wearable identity manager device from the wrist or neck of the user by opening a clasp, lock or buckle).

As stated previously, the wearable identity manager device may comprise a locking mechanism which provides a constant electric contact when it is closed (i.e., the internal circuit of conducting wires is closed while the wearable identity manager device is in a locked configuration). Furthermore, as soon as the lock is opened, the circuit is broken. This is used to detect when the wearable identity manager device is potentially becoming worn by a user—i.e., when the clasp is closed—and when it is being removed from a user—i.e., when the clasp is opened. While it is possible to close the clasp without wearing the wearable identity manager, just as it is possible to continue wearing the wearable identity manager while briefly opening the lock and then closing it, the lock may nonetheless facilitate determining when the wearable identity manager device is changing states—between potentially worn to not likely worn. It is also possible to use a lock with a magnetic component to improve the connection when it is closed; or alternatively, a threaded lock that is opened and closed by screwing it on, where the threaded part is made of a material that conducts electricity.

In an alternative implementation, a clasp comprises a magnet and a circuit that detects changes in the magnetic field, which occurs when the clasp is opened. A person skilled in the art will appreciate that yet other variants are anticipated, wherein the lock or clasp detects being or becoming opened, and/or being or becoming closed. Other alternative approaches comprise sensors configured to determine when the wearable identity manager device is being physically associated and/or disassociated with a user. Possible implementations include using pressure sensors, temperature sensors, heartbeat sensors, and similar types of sensors that can be used to determine the likely proximity to a person.

Upon attaching the wearable identity manager device to his/her wrist, a user may complete the association process in any of various ways. For instance, the user may be required to enter a password via a user interface on the wearable identity manager device. However, if the wearable identity manager device does not have a user interface, the association may be completed by pairing the wearable identity manager device, at act 420, to a pairing device that does have a user interface. Such a pairing process may associate the wearable identity manager device with any of various types of devices including, for example, a mobile device, a personal computer, a pair of glasses with a screen, or other device with a user input/output (I/O) mechanism, such as a screen, a keyboard, a pointer, a button, a microphone, a speaker, a point-of-sale device or computer controlling a door lock, or a combination of such user I/O components. For simplicity, such a device is sometimes referred to infra as a "pairing device" and/or "associating device".

Figure 5:
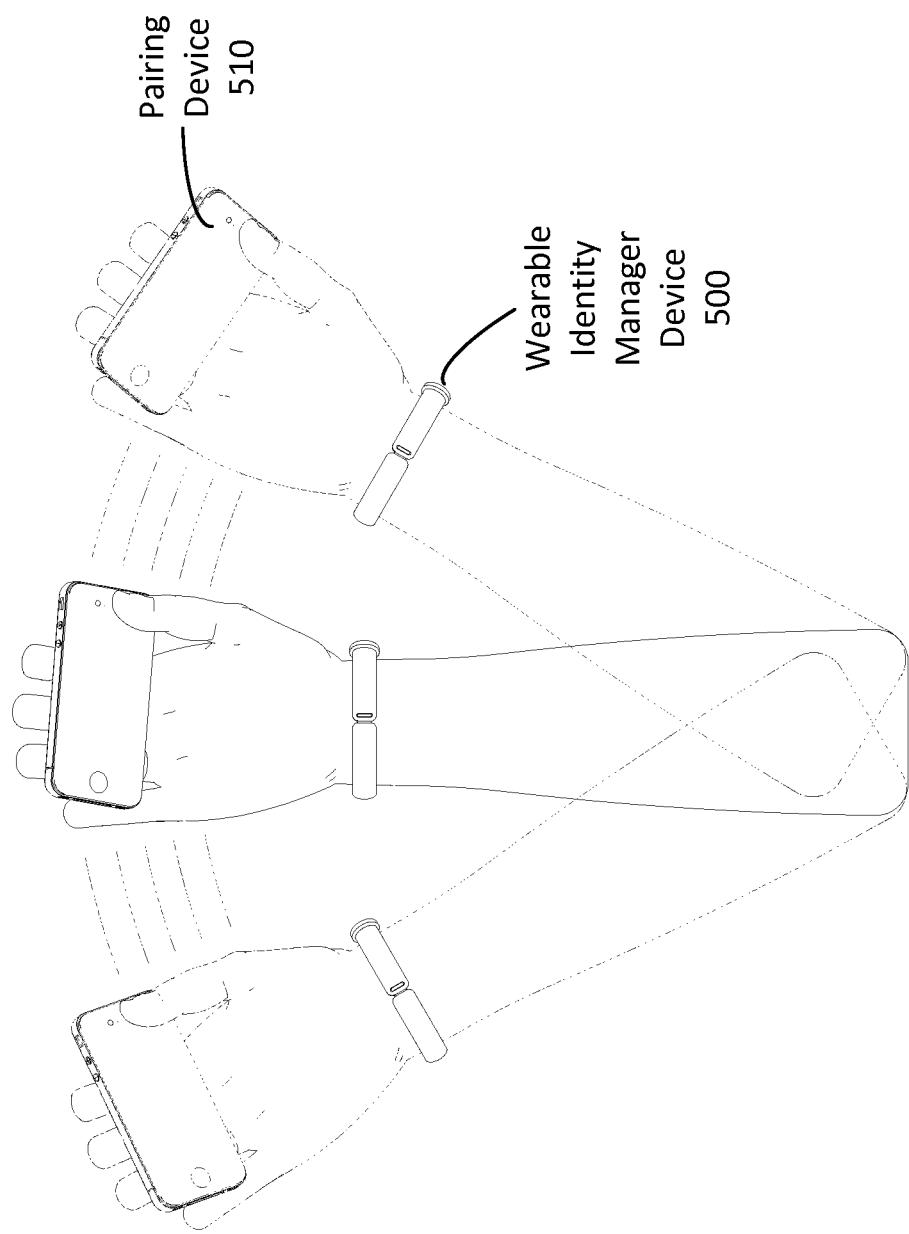
FIG. 5 is a schematic of an exemplary wearable identity manager device paired with a pairing device in accordance with an aspect of the disclosure.

Process 400 concludes at act 430 where the user is authenticated for a transaction. In a particular aspect of the disclosure, it is contemplated that such authentication process is facilitated by a user action. For instance, when the authentication process is started, the wearable identity manager device may communicate with an associated pairing device using built-in radio transmitters. If the wearable identity manager device has been paired with multiple devices, then one is selected, e.g., based on proximity or a user indication of intent. For example, as illustrated in FIG. 5, such intent may comprise moving both the wearable identity manager device 500 and the pairing device 510 in a synchronized manner. Other contemplated indications may include tapping the wearable identity manager device 500 and the pairing device 510 together, placing them in very close proximity, etc. Once a pairing device has been selected, pairing confirmation may be conveyed to the user via a signal emitted by the pairing device; such as tactile feedback, the display of an image, or the emission of a sound.

In another aspect of the disclosure, the engagement of a password manager is contemplated, wherein such engagement may be performed after the wearable identity manager device has selected a pairing device, as described above. In one implementation, the pairing device comprises the password manager, and the selection of the pairing device causes an unlock signal to be sent from the wearable identity manager device to the pairing device, after which the password manager determines the context of the authentication and performs a look-up of a user identity and credential associated with the context, where applicable. For example, the context may comprise a log-in screen to a financial service provider, including an associated domain. The password manager comprises at least one user profile, where a user profile is associated with one user or one persona (such as the user at home; the user at work, etc.). Based on the identity associated with the wearable identity manager device, one or more user profiles is selected, and based on contextual information, such as geographical location, user input, network identifiers, etc., a further selection among the one or more selected user profiles is performed. The password manager then determines, based on the context, such as the domain of the log-in screen, what account is to be selected. Alternatively, the user selects this using a user interface associated with the pairing device.

When an account has been selected, the associated user name and credential is used to perform a login or other authentication transaction. One example of a credential is a password; another is a personal identification number (PIN); another is a cryptographic key; and yet another is a collection of challenge questions and the associated answers. In an exemplary implementation, after the log-in session has completed, the session is transferred to another computational entity, such as a desktop computer, a door lock, or a point-of-sale device, where the user completes the session and initiates a log-out. In another implementation, the session is completed on the pairing device without being transferred.

Alternatively, the wearable identity manager device comprises the password manager, and performs a login as described above. Thereafter, the session optionally is transferred to another computational device, or in some instances, a credential or an unlock signal is communicated from the wearable identity manager device to the pairing device.

In yet another aspect, the wearable identity manager device communicates to an enrolled station, such as a door lock or a point-of-sale register instead of the pairing device. Within such an implementation, an enrolled station is associated with a computational device that has been paired with the wearable identity manager device. An unlock signal may comprise a sequence of bits that are generated by a generator of signals, such as a pseudo-random sequence generator or an approximation of such a function; so as to block replay attacks. The same sequence, or selected portions thereof, may be generated by the wearable identity manager device and a verifier associated with the enrolled station. It is well-known in the art how to synchronize an authentication token and a verifier, and these techniques can be used to synchronize the wearable identity manager device and the verifier, which is associated with the enrolled station.

The use of different user involvement to signal different types of approval is also contemplated. For instance, a first type of user involvement is no involvement at all. A first example of this is an enterprise scenario where the identity of a user is determined before the user is allowed into a corporate building. A second example is for toll charges as a user drives his/her car onto a toll road. There, a toll booth is establishing contact with the user's phone as he/she approaches, and the user's phone interacts with the user's wearable identity manager device to confirm the identity of the user. The same process may then be performed as the user leaves the toll way in order to determine the exact stretch of the road that the user should be billed for accessing. If a user does not have a wearable identity manager device, phone, or otherwise, the protocol does not successfully complete. Then, a toll may be charged in an alternative way, e.g., by using a photo taken of the license plate to bill the proper user.

A second type of user involvement is one that signals logging in. For instance, synchronously motioning a paired device and a wearable identity manager device, as illustrated in FIG. 5, may be used. Here, the user may have to continue making motions until a sufficiently strong motion has been registered for both the pairing device and the wearable identity manager device, and these two motions have been determined to strongly correlate to each other. An exemplary motion associated with logging in is a horizontal swipe, mimicking how some phones are currently unlocked.

A third type of user involvement is one that signals a purchase approval. An example is a pre-defined up-down-up shake with the hand, followed by pressing an approval button on the pairing device. Additional types of user involvement can be added, including the use of different user involvement types to help disambiguate different types of actions to users, help create confirmations where beneficial, and help simplify the user experience where this is more important than recording explicit confirmation. Another exemplary motion associated with payment is a vertical swipe, mimicking the swiping of a credit card.

In a further aspect of the disclosure, the wearable identity manager device may provide keys used to decrypt resources. For example, a user may elect to have the entire memory hierarchy of his/her device automatically encrypted when the device is at rest or a sudden event takes place, such as the device experiencing an unusual acceleration. Another user may elect to have only selected portions, such as the mail folder and address book, automatically encrypted, and only when the device is turned off or when it is not used for a period exceeding a threshold amount of time. The only way to access memory areas that have been encrypted may be to decrypt them with the key, which is kept by the wearable identity manager device and only released under controlled conditions. For instance, a rule may be implemented in which the key is only released when the device to be unlocked is in its presence, and only if the user performs a waving motion specific to unlocking the device. This protects pairing devices against theft and unwanted use.

It should also be appreciated that the wearable identity manager device may be associated with a long-term access credential the first time it is used, wherein such credential may be stored within the wearable identity manager. As the wearable identity manager device is associated with a pairing device, the user of the pairing device enters a long-term access credential, which is transmitted to the wearable identity manager device (e.g., via a secured connection, as what is typically afforded by secure modes of operation of Bluetooth, near-field, or WiFi). The transmitted credential is compared with the stored credential and it is determined whether they match. If there is a match, then the wearable identity manager device accepts the request to associate itself with the pairing device. The wearable identity manager device optionally stores multiple independent long-term access credentials, which are associated with different users; the corresponding persona or stored set of credentials are made accessible by the correct authentication using one of these long-term credentials. A password, PIN, or similar credential can be used as a long-term credential. Alternatively, a biometric template can be stored to support biometric authentication. After a successful association, but before a corresponding disassociation, a user can send a command to the wearable identity manager device from the pairing device, to add another profile and associated long-term credential; or to modify or erase a long-term credential.

In yet another aspect of the disclosure, the hardware associated with the wearable identity manager device comprises a biometric sensor, such as a fingerprint sensor, a microphone used to identify the voice of a user, or other such sensor. Whereas in a typical commercial deployment, the tradeoff between speed of operation and reduction of error rates commonly result in relatively low security or high sensor cost, the described disclosure would not require frequent user authentication, but only at the association phase when the wearable identity manager device is being associated with the user. Therefore, it is possible to place much higher requirements of a fit between a biometric sensor reading and a stored template. As a result, one can reduce the error rate or the cost of the biometric sensor hardware, or both, while still achieving excellent usability: it is only when the user starts to wear the wearable identity manager device that he or she needs to authenticate. Whereas a regular biometric authentication may be undesirable if it takes more than a split second for the user to operate, a typical user may tolerate a much more involved authentication in this context. This is both since the association is less frequent, and because it is not typically performed at a time when the user is hurried to reach a goal, such as completing a transaction. For the same reason, it may also be acceptable to use an intricate knowledge-based or recall-based authentication method instead of the described biometric authentication method, which therefore allows increased security, or the choice of authentication methods that have higher recall rates than typical passwords do.

In another contemplated implementation, a wearable identity manager device is associated with an account or a pseudonym instead of a user identity, or carries a representation of funds that are disbursed or committed to by user actions as described for other implementations herein.

Exemplary Hardware Implementation

Figure 6:
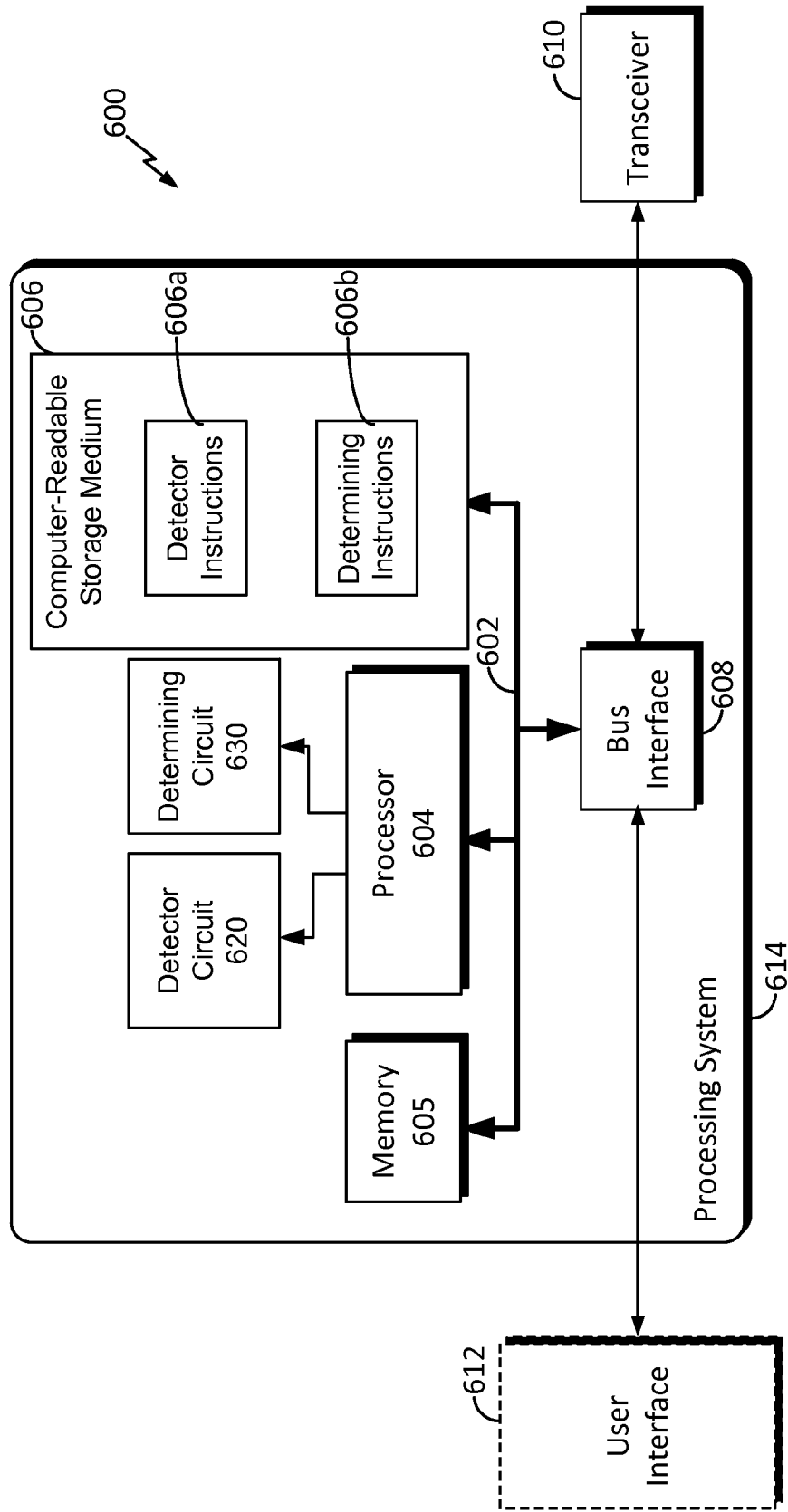
FIG. 6 is a block diagram illustrating an example of a wearable identity manager device employing a processing system according to some aspects of the disclosure.

Referring next to FIG. 6, a conceptual diagram illustrating an exemplary hardware implementation for a wearable identity manager device 600 employing a processing system 614 is provided, wherein wearable identity manager device 600 may be implemented within any radio-enabled device including, for example, any of the wearable identity manager devices discussed with reference to FIGS. 1-5. In accordance with various aspects of the disclosure, an element, or any portion of an element, or any combination of elements may be implemented with a processing system 614 that includes one or more processors 604. Examples of processors 604 include microprocessors, microcontrollers, digital signal processors (DSPs), field programmable gate arrays (FPGAs), programmable logic devices (PLDs), state machines, gated logic, discrete hardware circuits, and other suitable hardware configured to perform the various functionality described throughout this disclosure. That is, the processor 604, as utilized in wearable identity manager device 600, may be used to implement any one or more of the processes described below and illustrated in FIG. 6.

In this example, the processing system 614 may be implemented with a bus architecture, represented generally by the bus 602. The bus 602 may include any number of interconnecting buses and bridges, including a service oriented architecture (SOA) bus, depending on the specific application of the processing system 614 and the overall design constraints. The bus 602 links together various circuits including one or more processors (represented generally by the processor 604), a memory 605, and computer-readable media (represented generally by the computer-readable medium 606). The bus 602 may also link various other circuits such as timing sources, peripherals, voltage regulators, and power management circuits, which are well known in the art, and therefore, will not be described any further. A bus interface 608 provides an interface between the bus 602 and a transceiver 610. The transceiver 610 provides a means for communicating with various other apparatus over a transmission medium. Depending upon the nature of the apparatus, a user interface 612 (e.g., keypad, display, speaker, microphone, joystick) may also be provided.

In an aspect of the disclosure, computer-readable medium 606 is configured to include various instructions 606a and/or 606b to facilitate authenticating a user via a wearable identity manager device, as shown. In a similar aspect, such authenticating can instead be implemented via hardware by coupling processor 604 to any of circuits 620 and/or 630, as shown. Moreover, it is contemplated that the authenticating may be performed by any combination of instructions 606a and/or 606b, as well as any combination of circuits 620 and/or 630. In a particular aspect of the disclosure, instructions 606a and circuit 620 are directed towards a detector component configured to determine an association status between a user and wearable identity manager device 600 based on whether wearable identity manager device 600 is worn by the user, whereas instructions 606b and circuit 630 are directed towards a determining component configured to facilitate determining a user authentication.

To this end, it should be appreciated that wearable identity manager device 600 may be configured to facilitate user authentications in any of various ways. In a first aspect, such authentication comprises utilizing motion data tracked by wearable identity manager device 600 to validate a user's identity (e.g., waving a user's hand to validate a vending machine transaction). For this particular implementation, instructions 606*b* and/or circuit 630 may further comprise a sensor component configured to monitor motion data associated with a movement of wearable identity manager device 600. Transceiver component 610 may then be configured to transmit the motion data (e.g., to a vending machine) based on the association status, together with other authentication data (e.g., payment information).

In a second aspect, user authentication is contemplated via a pairing device (e.g., via pairing device 330). Here, it is contemplated that such pairing device may serve as a proxy device, wherein authentication data provided by wearable identity manager device 600 to the pairing device facilitates a user authentication requested by an external device (e.g., a PoS terminal) via the pairing device. For this implementation, instructions 606*b* and/or circuit 630 may further comprise a pairing component configured to pair wearable identity manager device 600 with a pairing device. Transceiver component 610 may then be configured to transmit authentication data (e.g., payment information) to the pairing device based on the association status.

Referring back to the remaining elements of FIG. 6, it should be appreciated that processor 604 is responsible for managing the bus 602 and general processing, including the execution of software stored on the computer-readable medium 606. The software, when executed by the processor 604, causes the processing system 614 to perform the various functions described below for any particular apparatus. The computer-readable medium 606 may also be used for storing data that is manipulated by the processor 604 when executing software.

One or more processors 604 in the processing system may execute software. Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium 606. The computer-readable medium 606 may be a non-transitory computer-readable medium. A non-transitory computer-readable medium includes, by way of example, a magnetic storage device (e.g., hard disk, floppy disk, magnetic strip), an optical disk (e.g., a compact disc (CD) or a digital versatile disc (DVD)), a smart card, a flash memory device (e.g., a card, a stick, or a key drive), a random access memory (RAM), a read only memory (ROM), a programmable ROM (PROM), an erasable PROM (EPROM), an electrically erasable PROM (EEPROM), a register, a removable disk, and any other suitable medium for storing software and/or instructions that may be accessed and read by a computer. The computer-readable medium may also include, by way of example, a carrier wave, a transmission line, and any other suitable medium for transmitting software and/or instructions that may be accessed and read by a computer. The computer-readable medium 606 may reside in the processing system 614, external to the processing system 614, or distributed across multiple entities including the processing system 614. The computer-readable medium 606 may be embodied in a computer program product. By way of example, a computer program product may include a computer-readable medium in packaging materials. Those skilled in the art will recognize how best to implement the described functionality presented throughout this disclosure depending on the particular application and the overall design constraints imposed on the overall system.

Figure 7:
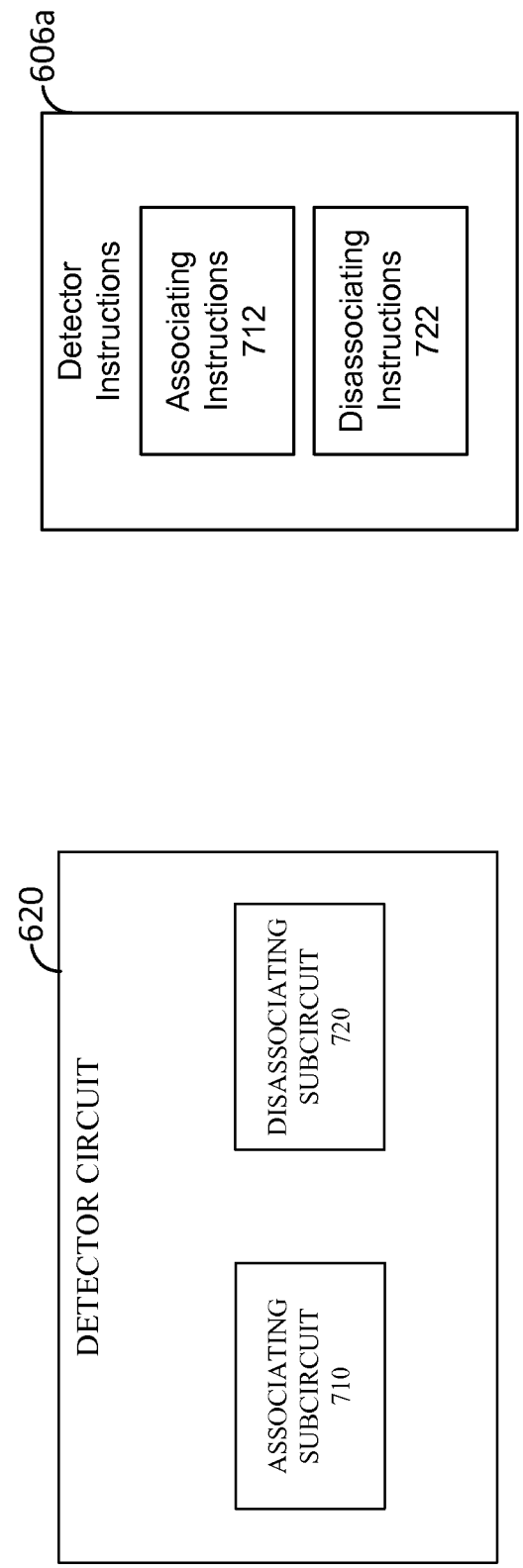
FIG. 7 is a block diagram illustrating exemplary detector components according to an aspect of the disclosure.

Referring next to FIG. 7, it should be appreciated that each of detector circuit 620 and detector instructions 606*a* may facilitate ascertaining an association status of a user with wearable identity manager device 600 via any of a plurality of subcomponents. For instance, detector circuit 620 may comprise associating sub-circuit 710, and disassociating sub-circuit 720, whereas detector instructions 606*a* may comprise associating instructions 712, and disassociating instructions 722. Here, associating sub-circuit 710 and associating instructions 712 are directed towards initially associating a user with wearable identity manager device 600 via an association procedure. It is contemplated that such association procedure can either be performed via wearable identity manager device 600 directly (e.g., via a user interface) or via an associating device (e.g., via pairing device 330). In a particular aspect of the disclosure, associating sub-circuit 710 and/or associating instructions 712 may be configured to match a locally stored password with a password input by the user via wearable identity manager device 600 and/or the associating device. In another aspect of the disclosure, associating sub-circuit 710 and/or associating instructions 712 may be configured to match data corresponding to an associating movement of wearable identity manager device 600 with data received from the associating device corresponding to a movement of the associating device. Alternatively, rather than comparing a movement of wearable identity manager device 600 to a movement of an associating device, the movement of wearable identity manager device 600 can be compared to internally stored data corresponding to a predetermined associating movement (e.g., waving wearable identity manager device 600 from side to side).

Figure 8:
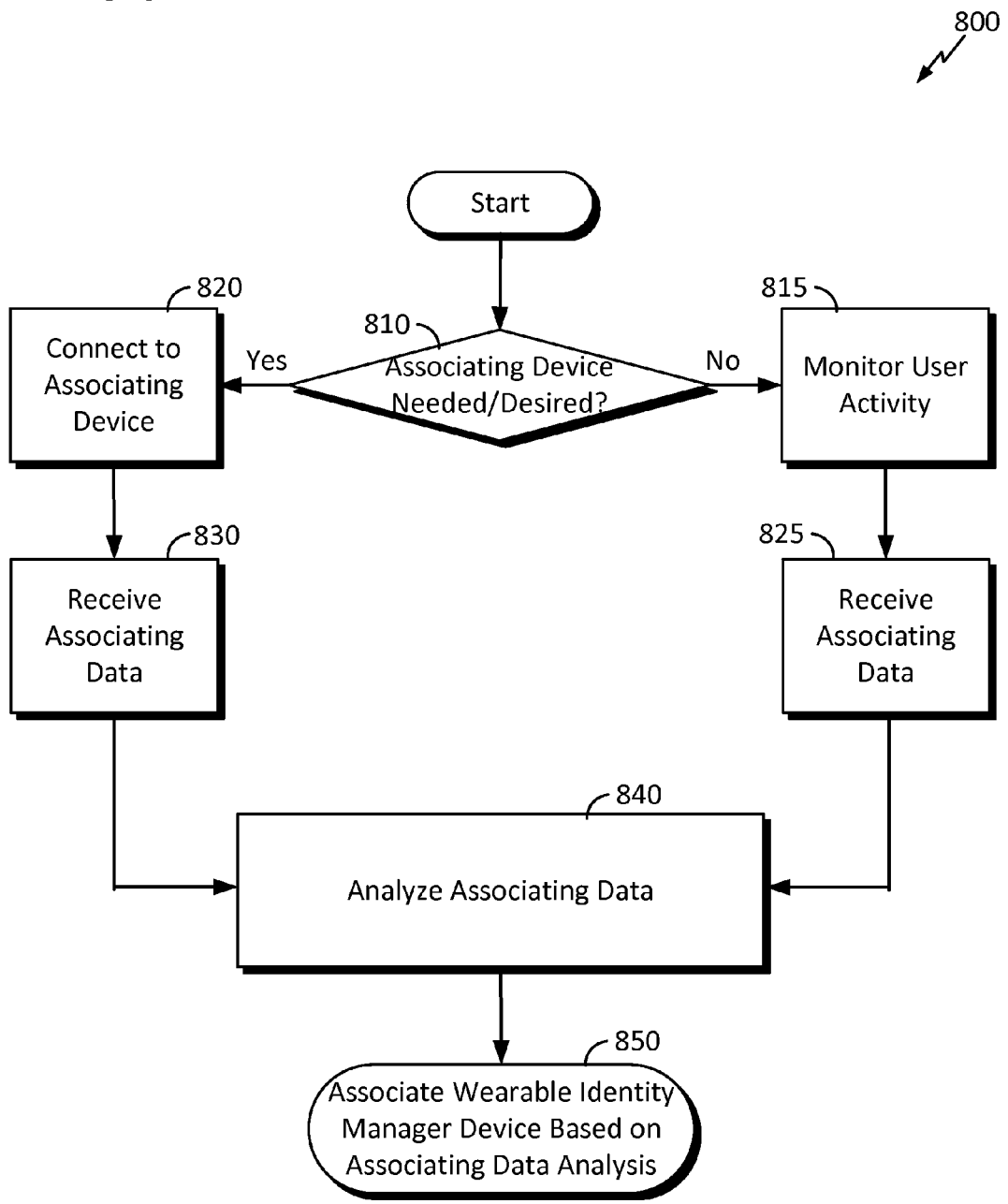
FIG. 8 is a flow chart illustrating an exemplary process to facilitate associating a user with a wearable identity manager device according to some aspects of the disclosure.

Referring next to FIG. 8, a flowchart illustrating an exemplary process 800 to facilitate associating a user with a wearable identity manager device is provided. In an aspect of the disclosure, it is contemplated that procedure 800 may be performed by wearable identity manager device 600 via associating sub-circuit 710 and/or associating instructions 712. Procedure 800 begins at act 810 where wearable identity manager device 600 determines whether an associating device is needed.

It should be appreciated that several implementations for associating a user without an associating device are contemplated. For instance, if an associating device is not needed/desired, procedure 800 proceeds to act 815 where user activity is monitored for associating data. To this end, it should be appreciated that such associating data may comprise any of various types of data associated with a user action including, for example, a password input (e.g., entered via a keyboard), a voice command (e.g., received via a microphone, and/or a movement (e.g., tracked by an accelerometer). Once the associating data is received at act 825, procedure 800 proceeds to act 840 where the associating data is analyzed (e.g., comparing an inputted password to an internally stored password). Procedure 800 then concludes at act 850 where an association status is determined based on the analysis (e.g., based on whether the inputted password matches the internally stored password).

In many instances, however, an associating device is indeed needed/desired. For example, since wearable identity manager device 600 may lack a user interface to enter a password, utilizing an associating device that has a user interface may be required. Even if wearable identity manager device 600 includes a user interface, the form factor of such interface could make entering a password cumbersome.

Referring back to procedure 800, if an associating device is thus indeed needed/desired at act 810, wearable identity manager device 600 then proceeds to act 820 where a connection is established with the associating device. Here, it should be appreciated that such connection may be a wireless connection (e.g., via a Bluetooth connection) or a wired connection (e.g., via a universal serial bus connection). Once connected, wearable identity manager device 600 may then begin to receive associating data from the associating device at act 830, which is then analyzed at act 840 (e.g., comparing a received password to an internally stored password). Procedure 800 then concludes at act 850 where an association status is determined based on the analysis (e.g., based on whether the received password matches the internally stored password).

Also, for authentications requiring a more secure association procedure (e.g., purchases exceeding a threshold amount, sensitive e-mail accounts, etc.), it may be desirable to utilize data ascertained via both wearable identity manager device 600 and an associating device. For instance, similar to wearable identity manager device 500 discussed with reference to FIG. 5, an association procedure may comprise synchronously motioning the associating device and wearable identity manager device 600, wherein the associating data received at act 830 comprises motion data from both wearable identity manager device 600 and the associating device. At act 840, the respective movements of the associating device and wearable identity manager device 600 are then compared based on this motion data. If the movements are deemed to be substantially similar (e.g., in time and path traversed), the user is then associated to wearable identity manager device 600 at act 850.

Referring back to FIG. 7, as illustrated, detector circuit 620 may further comprise disassociating sub-circuit 720, whereas detector instructions 606*a* may further comprise disassociating instructions 722. Here, disassociating sub-circuit 720 and disassociating instructions 722 are directed towards disassociating a user from wearable identity manager device 600 upon detecting that wearable identity manager device 600 is no longer worn by the user. In a particular aspect of the disclosure, wearable identity manager device 600 may be coupled to one or more sensor components, wherein disassociating sub-circuit 720 and/or disassociating instructions 722 may be configured to infer whether wearable identity manager device 600 is worn based on data retrieved from such sensors. To this end, it should be appreciated that any one or more of various types of sensor components may be used including, for example, a clasp sensor (e.g., to detect when a bracelet, such as wearable identity manager device 100, has become unlocked), a pressure sensor (e.g., to detect pressure between a ring and a finger), a temperature sensor (e.g., to detect body temperature), a pulse sensor (e.g., to detect a heartbeat), or a stretch sensor (e.g., to detect when a stretchable bracelet has been stretched).

Figure 9:
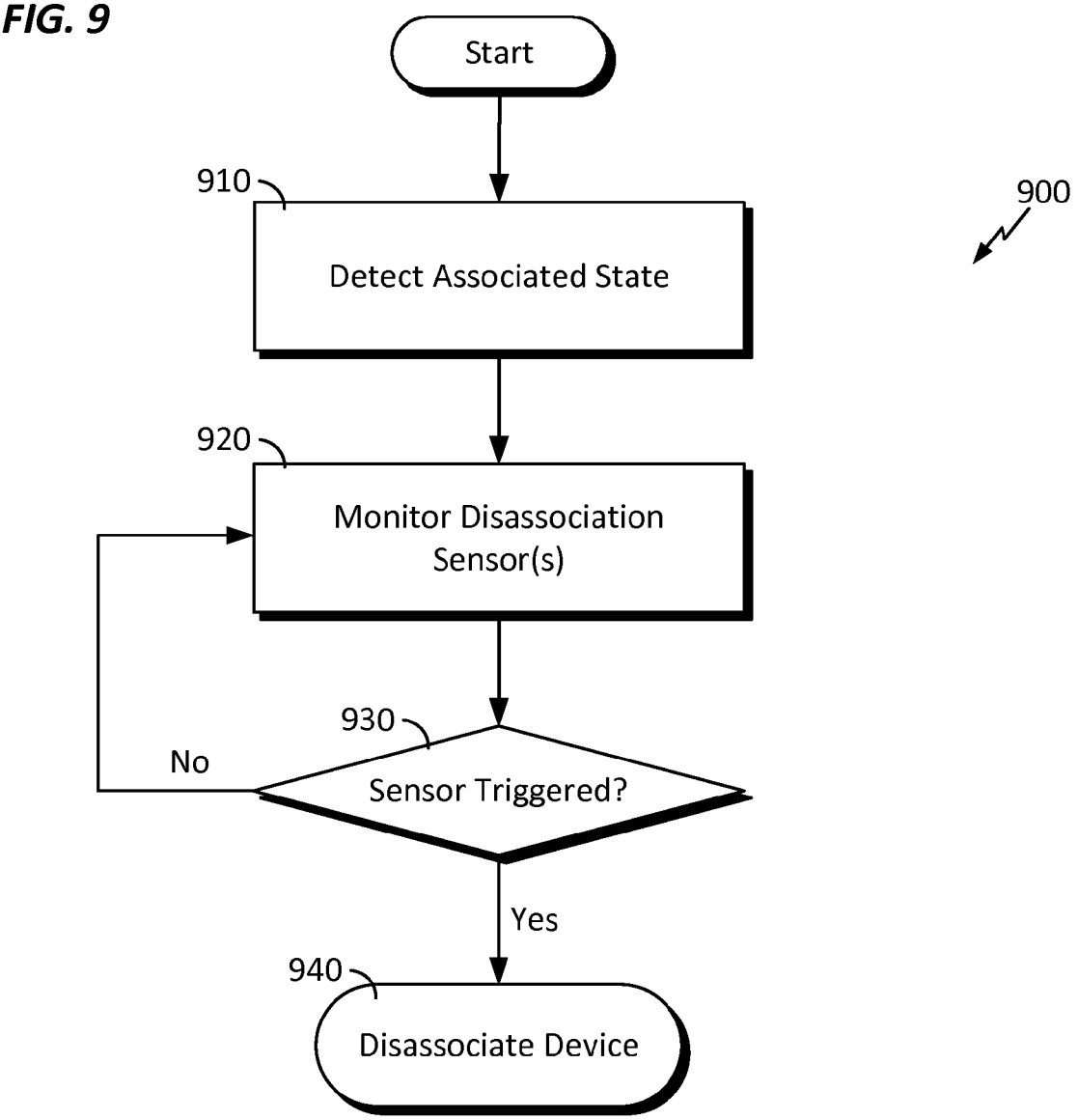
FIG. 9 is a flow chart illustrating an exemplary process to facilitate disassociating a user from a wearable identity manager device according to some aspects of the disclosure.

Referring next to FIG. 9, a flowchart illustrating an exemplary process 800 to facilitate disassociating a user from a wearable identity manager device is provided. In an aspect of the disclosure, it is contemplated that procedure 800 may be performed by wearable identity manager device 600 via disassociating sub-circuit 720 and/or disassociating instructions 722. Procedure 900 begins at act 910 with wearable identity manager device 600 detecting that it is in an associated state. Once wearable identity manager device 600 enters an associated state, procedure 900 proceeds to act 920 where disassociation sensors coupled to wearable identity manager device 600 are monitored. Here, as previously mentioned, such monitoring may comprise retrieving data from one or more of various types of sensors including, for example, a clasp sensor, a pressure sensor, a temperature sensor, a pulse sensor, or a stretch sensor. To this end, threshold values consistent with wearable identity manager device 600 being worn by a user may be assigned to particular disassociation sensors (e.g., a threshold pressure value, a threshold temperature value, etc.), wherein inferences as to whether wearable identity manager device 600 is being worn are based on comparing received sensor values to such thresholds. At act 930, wearable identity manager device 600 then determines whether any of the disassociation sensors have been triggered. If a disassociation sensor has indeed been triggered, process 900 concludes at act 940 with wearable identity manager device 600 becoming disassociated from the user. Otherwise, if a disassociation sensor is not triggered, process 900 loops back to act 920 where the disassociation sensors continue to be monitored.

Figure 10:
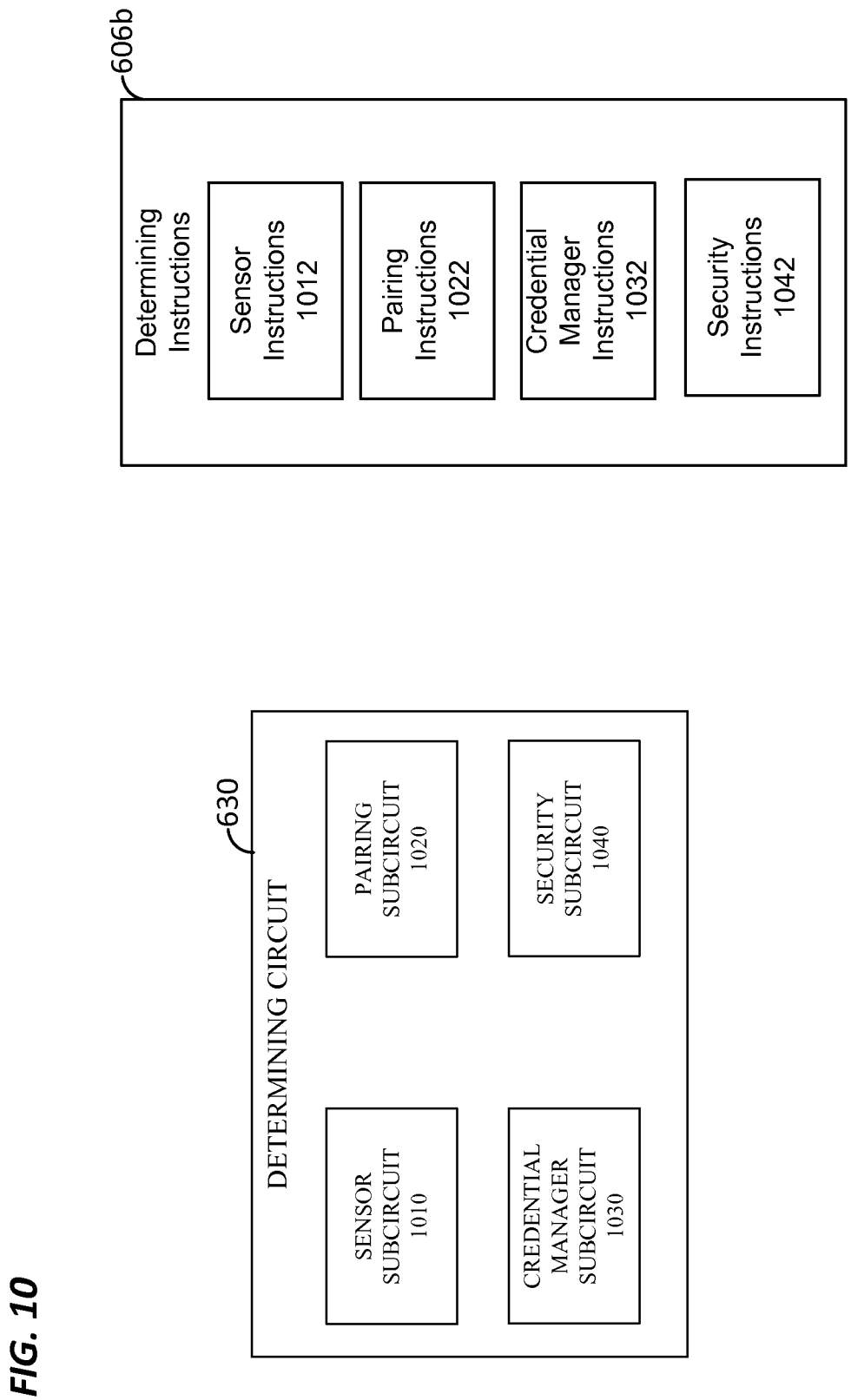
FIG. 10 is a block diagram illustrating exemplary determining components according to an aspect of the disclosure.

Referring next to FIG. 10, it should be appreciated that each of determining circuit 630 and determining instructions 606*b* may facilitate determining a user authentication via any of a plurality of subcomponents. For instance, determining circuit 630 may comprise sensor sub-circuit 1010, pairing sub-circuit 1020, credential manager sub-circuit 1030, and security sub-circuit 1040, whereas determining instructions 606*b* may comprise sensor instructions 1012, pairing instructions 1022, credential manager instructions 1032, and security instructions 1042. As previously stated, motion data corresponding to a path traversed by wearable identity manager device 600 may be utilized to authenticate a user (e.g., waving a user's hand to validate a vending machine transaction). Here, sensor sub-circuit 1010 and/or sensor instructions 1012 may be configured to monitor such motion data via any of a plurality of motion sensor devices (e.g., an accelerometer, gyro, etc.).

In a further aspect, it is contemplated that wearable identity manager device 600 may also be configured to utilize other types of data to authenticate a user. For instance, in addition to motion data corresponding to a movement undergone by wearable identity manager device 600, sensor sub-circuit 1010 and/or sensor instructions 1012 may be configured to retrieve data from one or more other components coupled to wearable identity manager device 600. Such components may, for instance, include a button (e.g., where authenticating may comprise pressing a touchscreen button while waiving the user's hand), a global positioning system (GPS) device (e.g., where authenticating may comprise confirming a location of the user while he/she waives), or a microphone (e.g., where authenticating may comprise saying a voice command while waiving the user's hand). Authentication data provided by wearable identity manager device 600 may thus include sensor data from any of these or other components, wherein such authentication data facilitates validating a user's identity to a requesting device (e.g., a PoS terminal, a pairing device, etc.).

Figure 11:
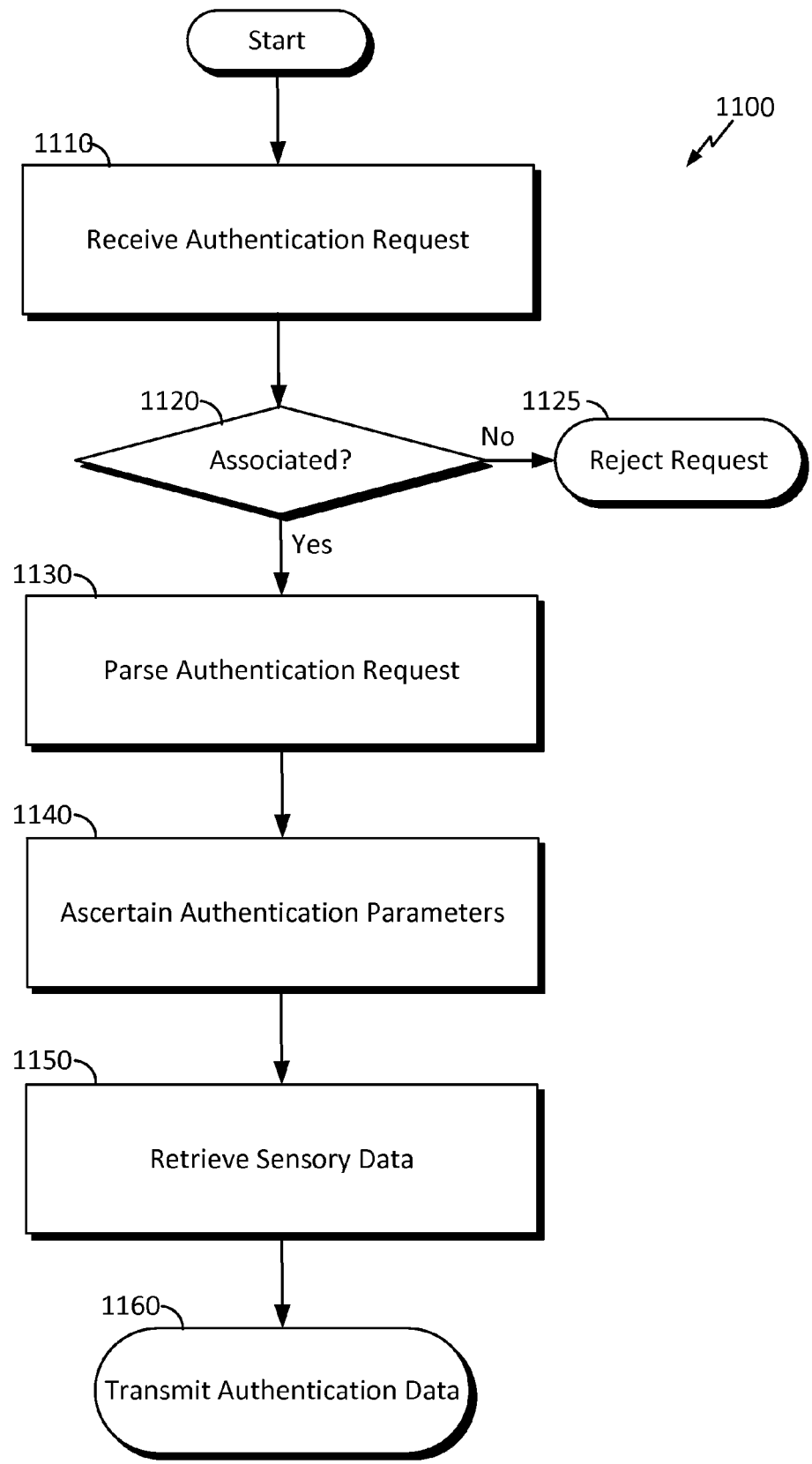
FIG. 11 is a flow chart illustrating an exemplary process in which sensory data is utilized to facilitate a user authentication according to some aspects of the disclosure.

Referring next to FIG. 11, a flowchart illustrating an exemplary process 1100 in which sensory data is utilized to facilitate a user authentication is provided. In an aspect of the disclosure, it is contemplated that procedure 1100 may be performed by wearable identity manager device 600. Procedure 1100 begins at act 1110 where wearable identity manager device 600 receives an authentication request.

Here, it is contemplated that such request may be received directly from a requesting entity (e.g., a PoS terminal) or indirectly from a requesting entity via a proxy device (e.g., a pairing device). Upon receiving the authentication request, procedure 1100 proceeds to act 1120 to determine whether wearable identity manager device 600 is associated with the user. If wearable identity manager device 600 is not associated with the user, procedure 1100 concludes with the authentication request being rejected at act 1125. Alternatively, rather than rejecting the request, wearable identity manager device 600 may be configured to only receive authentication requests while in an associated state.

However, if wearable identity manager device 600 is indeed associated with the user, procedure 1100 proceeds to act 1130 where the authentication request is parsed. By parsing the request, wearable identity manager device 600 is able to ascertain the various authentication parameters associated with the request at act 1140. At act 1150, wearable identity manager device 600 then retrieves sensory data corresponding to the particular authentication parameters identified in act 1140. For instance, whereas one authentication request may simply require motion data corresponding to an up and down movement, another authentication request may require motion data corresponding to an up and down movement plus a voice command. Wearable identity manager device 600 then transmits authentication data to the requesting entity at act 1160, wherein the authentication data includes the motion data.

Referring back to FIG. 10, as illustrated, determining circuit 630 may further comprise pairing sub-circuit 1020, whereas determining instructions 606b may further comprise pairing instructions 1022. Here, pairing sub-circuit 1020 and pairing instructions 1022 are directed towards pairing wearable identity manager device 600 with a pairing device (e.g., pairing device 330). Moreover, it is contemplated that pairing sub-circuit 1020 and/or pairing instructions 1022 may be configured to facilitate such pairing so that wearable identity manager device 600 may be used to authenticate user transactions initiated via the paired device.

Figure 12:
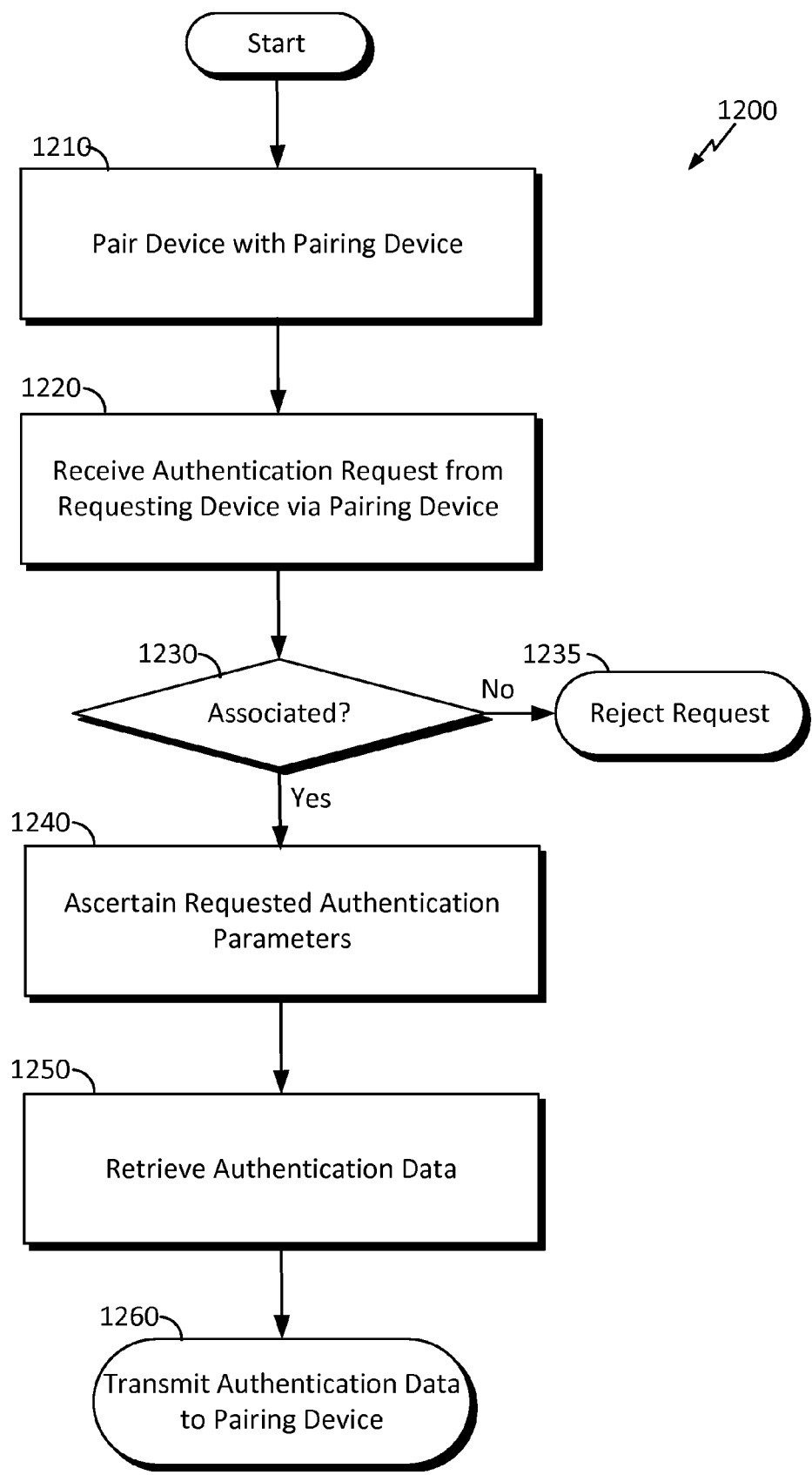
FIG. 12 is a flow chart illustrating an exemplary process in which a pairing device is utilized to facilitate a user authentication according to some aspects of the disclosure.

Referring next to FIG. 12, a flowchart illustrating an exemplary process 1200 in which a pairing device is utilized to facilitate a user authentication is provided. In an aspect of the disclosure, it is contemplated that procedure 1200 may be performed by wearable identity manager device 600. Procedure 1200 begins at act 1210 where wearable identity manager device 600 is paired with a pairing device. Next, at act 1220 wearable identity manager device 600 receives an authentication request from a requesting entity via the pairing device. For instance, if the transaction is an online purchase, the requesting entity is the online retailer, whereas the paired device is the device running the browser application (e.g., a laptop, smartphone, etc.). Upon receiving the authentication request, procedure 1200 proceeds to act 1230 to determine whether wearable identity manager device 600 is associated with the user. If wearable identity manager device 600 is not associated with the user, procedure 1200 concludes with the authentication request being rejected at act 1235.

However, if wearable identity manager device 600 is indeed associated with the user, procedure 1200 proceeds to act 1240 where the various authentication parameters associated with the request are ascertained. At act 1250, wearable identity manager device 600 then retrieves authentication data corresponding to the particular authentication parameters identified in act 1240. Wearable identity manager device 600 then transmits authentication data to the pairing device at act 1260, wherein such transmission eliminates the need for personal information to be manually entered via the pairing device to authenticate the user to the requesting entity.

Referring again to FIG. 10, as illustrated, determining circuit 630 may further comprise credential manager sub-circuit 1030 and security sub-circuit 1040, whereas determining instructions 606b may further comprise credential manager instructions 1032 and security instructions 1042. Here, credential manager sub-circuit 1030 and credential manager instructions 1032 are directed towards providing a credential associated with a user, whereas security sub-circuit 1040 and security instructions 1042 are directed towards ascertaining a security level associated with an authentication request. Moreover, it is contemplated that wearable identity manager device 600 may be configured to utilize any combination of credential manager sub-circuit 1030, credential manager instructions 1032, security sub-circuit 1040, and/or security instructions 1042 to limit an amount of user credentials provided to a requesting entity based on a security level ascertained from an authentication request. In a particular aspect of the disclosure, credentials are provided based on at least one of a user action or an execution context extrapolated from the authentication request, whereas the security level is ascertained according to at least one of a user preference setting, an execution context, or one or more historical execution contexts. Furthermore, as discussed in more detail below, the security level may be selected from a plurality of possible security levels.

Figure 13:
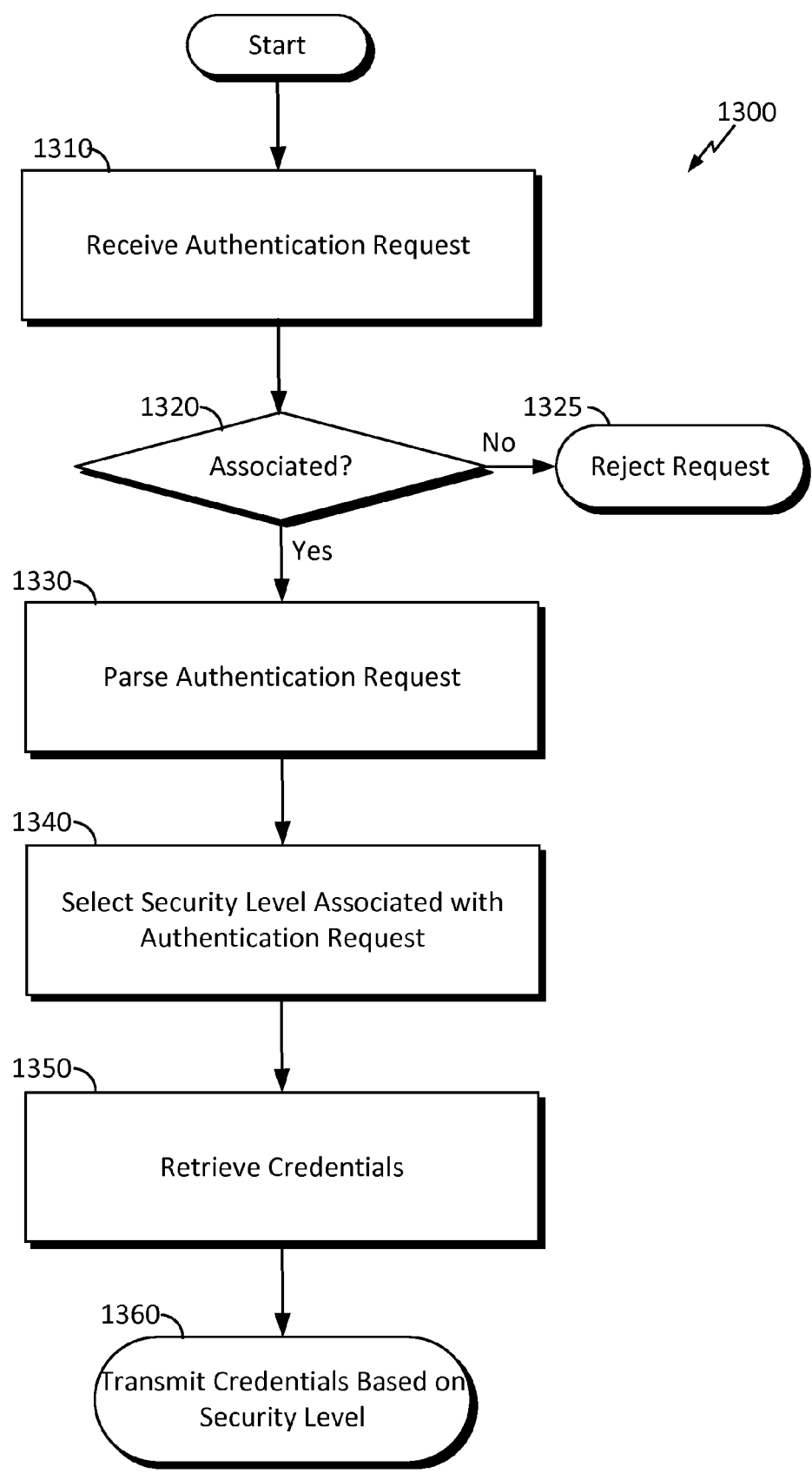
FIG. 13 is a flow chart illustrating an exemplary process in which credentials are transmitted according to an ascertained security level to facilitate a user authentication according to some aspects of the disclosure.

Referring next to FIG. 13, a flowchart illustrating an exemplary process 1300 in which credentials are transmitted according to an ascertained security level to facilitate a user authentication is provided. In an aspect of the disclosure, it is contemplated that procedure 1300 may be performed by wearable identity manager device 600. Procedure 1300 begins at act 1310 where wearable identity manager device 600 receives an authentication request. Upon receiving the authentication request, procedure 1300 proceeds to act 1320 to determine whether wearable identity manager device 600 is associated with the user. If wearable identity manager device 600 is not associated with the user, procedure 1300 concludes with the authentication request being rejected at act 1325.

However, if wearable identity manager device 600 is indeed associated with the user, procedure 1300 proceeds to act 1330 where the authentication request is parsed. By parsing the request, wearable identity manager device 600 is able to select an appropriate security level associated with the request at act 1340. As previously stated, such security level may be selected from a plurality of possible security levels, wherein the selection may depend on any of various factors (e.g., user preference setting, an execution context, and/or one or more historical execution contexts, etc.). At act 1350, wearable identity manager device 600 then retrieves credentials according to the security level selected in act 1340. Procedure 1300 then concludes at act 1360 with wearable identity manager device 600 transmitting the credentials to a requesting entity based on the security level.

Exemplary Levels of Security

It should be appreciated that the disclosed wearable identity infrastructure may facilitate any of various levels of security. In a particular aspect, however, three exemplary levels of security are contemplated: proximity verification, implicit assurance, and explicit confirmation. Each of these three levels of security, and corresponding pairing method, is discussed below, wherein pairing methods are described within the context of protocols between a station and the wearable identity manager device.

In this example, proximity verification is deemed the lowest of the three levels of security since it simply relies on verifying that an identity manager associated with an identity with access privileges is in the proximity of the object that the user interacts with (e.g., a phone, mouse, etc.). With respect to pairing, the station—whether phone, mouse, doorknob, point of sale terminal, etc.—may transmit a wake-up signal to the wearable identity manager device, who responds with an acknowledgment including a representation of the identity associated with the wearable identity manager device. This representation may be a static unique identifier, a pseudonym, the output from a rolling code, or a cryptographic token.

Figure 14:
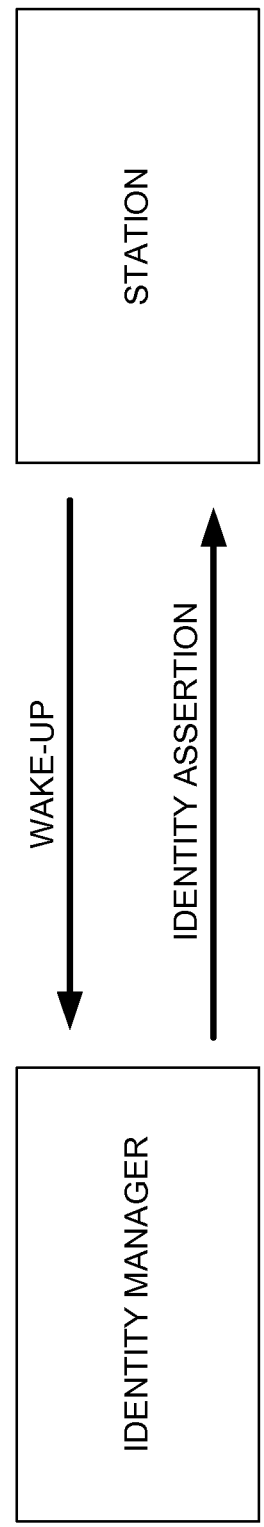
FIG. 14 is a schematic diagram illustrating an exemplary proximity verification between an identity manager and a station in accordance with an aspect of the disclosure.

Referring next to FIG. 14, a schematic diagram illustrating an exemplary proximity-based verification between a wearable identity manager and a station is provided. It is contemplated that, in the lowest security level, a proximity verification is sufficient to proceed with a transaction. In a particular implementation, the station transmits a wake-up signal that is received by the identity manager, causing it to respond with an identity assertion. The wake-up signal can include an indicator of the station's identity, which is compared to a whitelist kept by the identity manager. If there is a match, then an identity assertion is encrypted using a key associated with the station and the ciphertext transmitted to the station. Here, it should be noted that inferring the identity simply from a plain acknowledgment—in spite of the dedicated channel—is impossible since the station does not know whether the identify manager has been disassociated from its previous identity or not.

Of the three levels of security, implicit assurance is deemed the intermediate level. Implicit assurance relies on determining a plausible user intent for a user associated with an identity manager that passes the proximity verification. This can be obtained by comparing accelerometer data with data corresponding to implicit user actions (e.g., actions the user is taking without being requested to do so). Examples of such actions include tapping on a screen to select an application or resource, typing on a laptop keyboard, and turning a door knob. With respect to pairing, implicit assurance requires the comparison of two signals (e.g., two accelerometer traces, one accelerometer trace and an associated click timing signal, etc.). Such comparison may be carried out by the identity manager—which, in a sense, is responsible for correctly representing its user—and the result conveyed to the station, along with a representation of the identity associated with the identity manager, as described above.

The highest level of security is obtained from explicit user confirmation of an action, where the user's identity manager also has passed the proximity verification. Two examples of explicit confirmation are for a user to shake a phone (with the hand used to wear the smart bracelet), and signing on the screen of a point of sale terminal, where either the detected screen movements or the stylus accelerometer data is compared to the accelerometer data generated by the identity manager. The difference between implicit assurance and explicit confirmation, in terms of pairing, lies mostly in the certainty associated with the match obtained from the comparison of the two signals described above. Namely, for explicit confirmation, a greater amount of signal has to be compared. One practical implementation of the comparison of signals includes a simple form of entropy meter that determines the amount of likely entropy, adjusting for persistent background movement, and collecting a sufficient amount of signal before performing the comparison. Alternatively, the two signals can be compared (using a windowing method) until there is sufficient agreement, at which time a confirmation is generated and transmitted.

Figure 15:
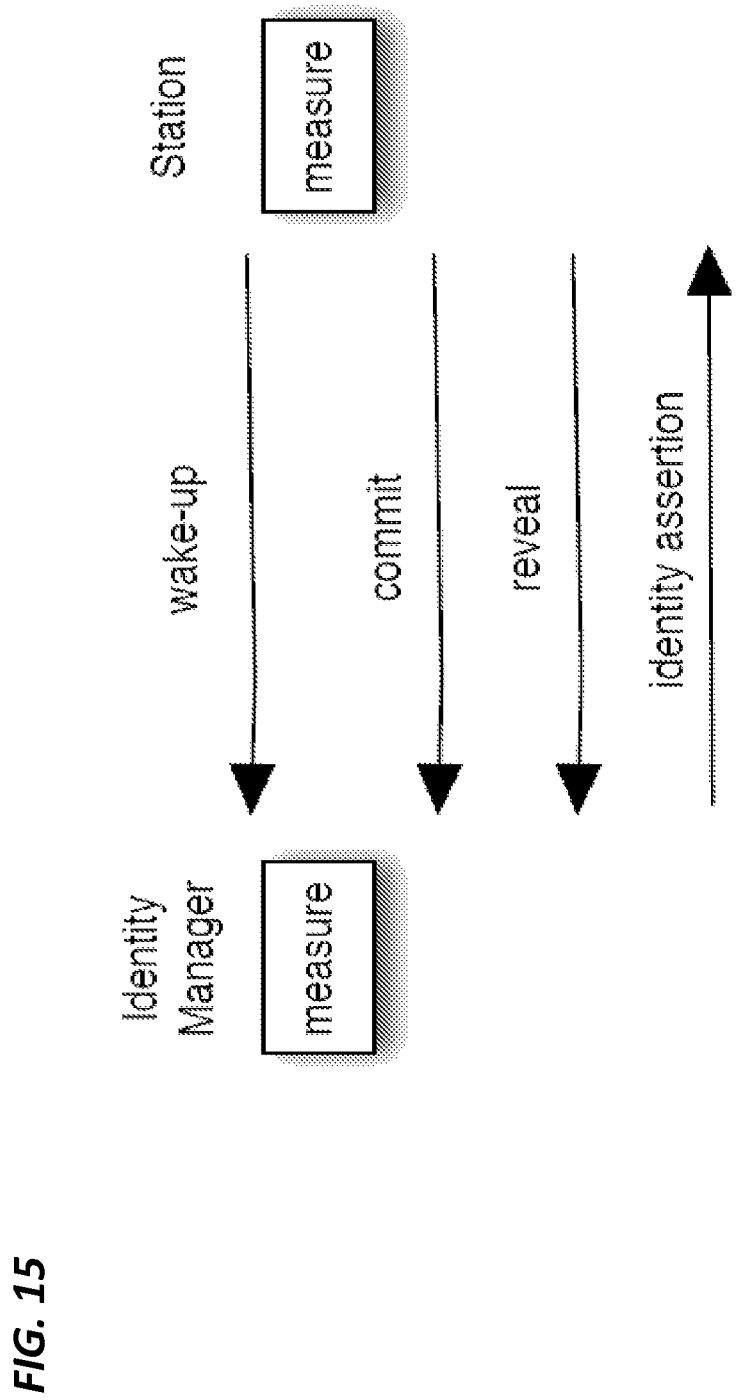
FIG. 15 is a schematic diagram illustrating an exemplary implicit assurance and explicit confirmation protocol between an identity manager and a station in accordance with an aspect of the disclosure.

In a particular aspect, it is contemplated that the security level can be adjusted to a desired level by selecting the type of task or the duration of it. Here, a protocol substantially similar to the implicit assurance protocol can be used, except that additional requirements are placed on the movements. Referring next to FIG. 15, an exemplary approach for implicit assurance and explicit confirmation is provided. The station starts by sending a wake-up signal. As soon as the identity manager receives the wake-up signal, it measures movements $m_1$. At the same time, the station measures movements $m_2$. Within a time period T of the wake-up signal, the station transmits a commitment to the measured movements $m_2$ and its public key P. The commitment can be computed by applying a cryptographic hash function to $m_2$, P and a number r that the station chooses at random. After the time T has elapsed from the wake-up signal, the station reveals the values ($m_2$; P; r). The identity manager verifies three facts: (1) that the commitment was received within time T of the wake-up signal; (2) that the commitment corresponds to the revealed values; and (3) that the movements $m_1$ and $m_2$ match each other sufficiently well. For explicit confirmation, it is also verified that the movements satisfy additional requirements. If all of these conditions are satisfied, then the identity manager prepares an identity assertion, encrypted using the public key P, and transmits the resulting ciphertext to the station.

Figure 16:
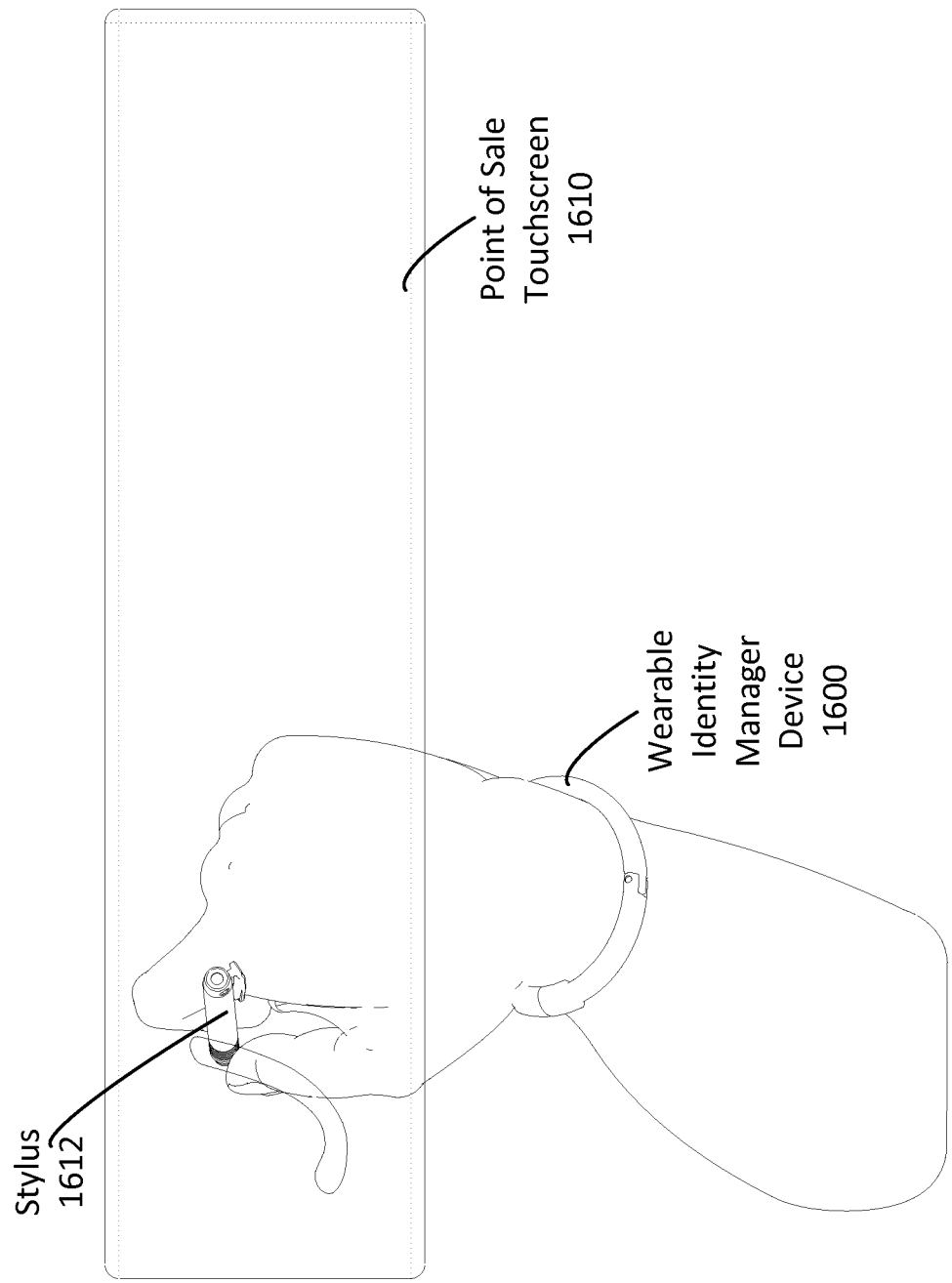
FIG. 16 is a first schematic illustrating an exemplary user authentication at a point of sale terminal in accordance with an aspect of the disclosure.
Figure 17:
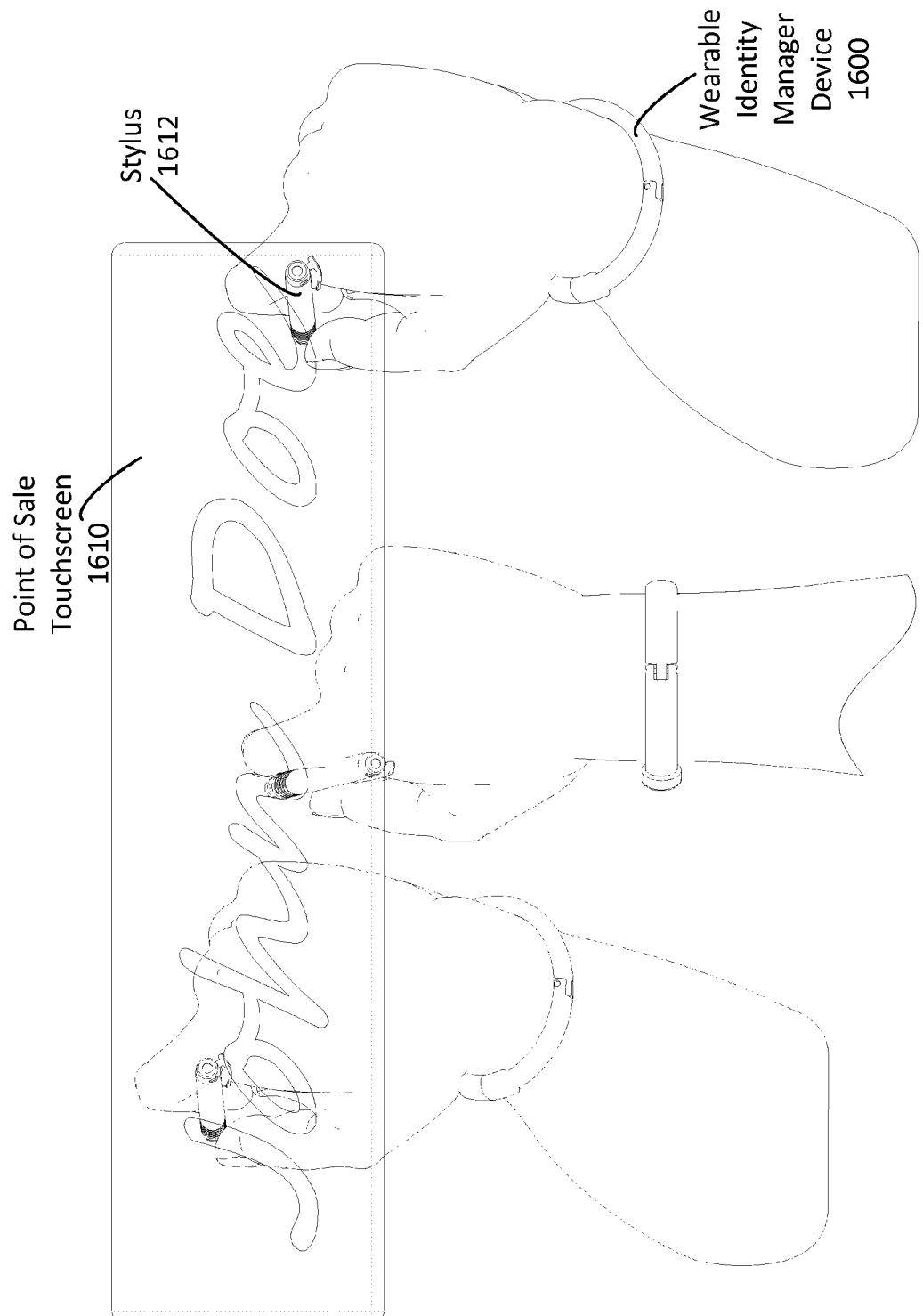
FIG. 17 is a second schematic illustrating an exemplary user authentication at a point of sale terminal in accordance with an aspect of the disclosure.

For many PoS transactions, it is noted that requiring a user signature may be the desired explicit confirmation. That is, user authentication for a PoS transaction may require the aforementioned matching of accelerometer data generated by an identity manager with detected PoS screen movements or stylus accelerometer data. Referring next to FIGS. 16-17, an exemplary signature authentication of a PoS transaction facilitated by a wearable identity manager device is provided. As illustrated in FIGS. 16-17, such authentication may require a user to sign his/her signature onto point of sale touchscreen 1610 with stylus 1612 while wearing wearable identity manager device 1600. In FIG. 16, for instance, initial strokes of a user's signature are shown, wherein accelerometer data generated by wearable identity manager device 1600 is matched with the initial strokes captured by point of sale touchscreen 1610 and/or accelerometer data corresponding to movements of stylus 1612. Moreover, a determination is made as to whether the detected path traversed by wearable identity manager device 1600 is consistent with signals corresponding to a signature stroke as detected by point of sale touchscreen 1610 and/or stylus 1612.

In some implementations, a contemporaneous detection of such signals and the path traversed by wearable identity manager device 1600 may be required. For instance, as illustrated in FIG. 17, a path traversed by wearable identity manager device 1600 as a user signs his/her name may be substantially horizontal, wherein such path is tracked from a time $t_1$ when the user begins to sign his/her name up to at time $t_2$ when the user finishes signing his/her name. Here, a substantially horizontal path of wearable identity manager device 1600 from $t_1$ to $t_2$ may be matched with signature strokes captured by point of sale touchscreen 1610 from $t_1$ to $t_2$ and/or accelerometer data corresponding to movements of stylus 1612 consistent with a signature from $t_1$ to $t_2$. Authentication of the PoS payment may then be based, at least in part, by confirming whether such match is within a predetermined degree of confidence.

Various exemplary authentications of PoS transactions in accordance with aspects disclosed herein are now described. In a first example, a user wears a wearable identity manager device on the wrist of his/her dominant hand, wherein it is assumed that the wearable identity manager device has been previously associated with the user, and thus already stores a representation of the user's identity. For this example, the PoS terminal is a legacy terminal comprising a screen with an associated stylus, and software used to record a time-based trace of the stylus on the screen. The PoS terminal is also connected to a network, and comprises a wireless radio transmitter. Here, the user starts by picking up the stylus, and places it close to the screen. As a result of this, an engage signal is transmitted using the wireless radio transmitter, which is received by the wearable identity manager device. The wearable identity manager device then enters a mode of operation associated with identification.

Next, the user is prompted to sign his/her name in a box on the PoS terminal screen. At the same time, the wearable identity manager device, having entered the mode of operation associated with identification, records the movement of the wearable identity manager device (e.g., via accelerometer data), which is temporarily saved in the form of a time-space series. Software on the PoS terminal then computes a function of the time-based trace of the stylus on the screen, and transmits it to the wearable identity manager device using the wireless radio transmitter.

The wearable identity manager device then makes a determination based on a comparison between the time-space series and the time-based trace, as to whether they correspond to each other within a predetermined degree of confidence. If it is determined that the two elements compare to each other, the wearable identity manager device enters a 'success' state. Otherwise, the wearable identity manager device remains in the same state for some threshold amount of time, potentially receiving additional signals and performing additional comparisons. If the time threshold is reached without the wearable identity manager device having entered the success state, it returns to the state it was in prior to the user picking up the stylus.

If the wearable identity manager device enters the success state, it communicates a success signal to the radio transmitter associated with the PoS terminal. In an exemplary implementation, this signal comprises information associated with one or more selections of financial resources that are associated with the user. If at least two selections are available, then the PoS screen is used to display these to the user, which allows the user to select his/her preferred source. Alternatively, such information is received from another repository.

It is contemplated that the success signal may further comprise identity information, and preferably an identity assertion that cannot be spoofed or replayed, such as a pseudonym associated with the wearable identity manager device or user identity, and a usage number or a time. In this example, information indicating the transaction amount and selected financial source is transmitted to a backend entity along with the identity information. The backend then determines what user should be charged what amount, and from what financial resource.

In a second exemplary usage scenario, many of the initial parameters disclosed above with respect to the first example are again assumed. Namely, it is assumed that a user wears a wearable identity manager device on the wrist of his/her dominant hand, wherein the wearable identity manager device has been previously associated with the user, and thus already stores a representation of the user's identity. A PoS terminal is again connected to a network and comprises a screen with an associated stylus, software used to record a time-based trace of the stylus on the screen, and a wireless radio transmitter. Once a user places a stylus close to the PoS screen, an engage signal is again transmitted to the wearable identity manager device, which causes it to enter a mode of operation associated with identification.

In this example, the stylus determines its movement using an accelerometer, wherein a signal including this accelerometer data is then sent to the wearable identity manager device, which is operating in a mode associated with identification. However, the wearable identity manager device also comprises an accelerometer, which generates a movement-based signal that is compared to the received stylus accelerometer signal. If these are determined to correspond to each other before some time threshold after the wearable identity manager device entered the identification mode, then the wearable identity manager device enters a success state. The system then proceeds according to the same procedure described in the first example above.

In a third example, a vending machine scenario is contemplated. Similar to the first and second examples, it is again assumed that a user wears a wearable identity manager device on the wrist of his/her dominant hand, wherein the wearable identity manager device has been previously associated with the user, and thus already stores a representation of the user's identity. The wearable identity manager device may further comprise an accelerometer, which can be used to track and record paths traversed by the wearable identity manager device.

In this example, a vending machine has a user interface detecting a user selection, and a radio transmitter configured to send an engage signal as a user approaches the vending machine. This engage signal is then received by the wearable identity manager device, which causes the wearable identity manager device to enter an identification mode. The vending machine then detects a user selection, and transmits a signal to the wearable identity manager characterizing the interaction, such as the timing and the acceleration data associated with the button or lever being engaged. A conventional point of sale device can also use this simplified user experience approach, of course, where a user simply has to click or wave, for example, to finalize a trans action.

Upon receiving the signal characterizing the interaction, in order to authenticate the user with this particular transaction, the wearable identity manager device compares the received signal to the internally stored accelerometer data corresponding to the path traversed by the wearable identity manager device. If there is such a correspondence detected before some time threshold after the time the wearable identity manager device entered the identification mode, then the wearable identity manager device enters a success state.

If the wearable identity manager device enters the success state, it communicates a success signal to the vending machine's radio transmitter. It is contemplated that such success signal may further comprise identity information, and preferably an identity assertion that cannot be spoofed or replayed, such as a pseudonym associated with the wearable identity manager device or user identity, and a usage number or a time. In this example, information indicating the transaction amount and selected financial source is transmitted by the vending machine to a backend entity along with the identity information. The backend then determines what user should be charged what amount, and from what financial resource.

Exemplary Benefits

One of ordinary skill will readily appreciate that various benefits may be achieved by implementing aspects disclosed herein. A non-exhaustive list of exemplary benefits is provided below.

A first exemplary benefit is that users are protected against phishing attacks, since users will not be in the habit of using any credentials (other than possibly to authenticate to their identity managers as these are associated with them). Users will also be protected from such attacks, since the identity manager will not convey any traditional credentials to a station that requests an authentication.

Another exemplary benefit is that users are protected—to some extent—against malware. This is because the very constrained interface between the identity manager and its surroundings makes it more difficult for the identity manager to be corrupted. In particular, since users are unlikely to install any software on their identity managers, an entire class of vulnerabilities is avoided.

A further benefit of the aspects disclosed herein is with respect to weak credentials. Namely, the quality of credentials becomes less of an issue, since credentials are only used in the association stage. This limits the potential use of weak credentials to people with physical access to a targeted identity manager.

Also, if either the identity manager or an associated proxy acts as a password manager, this also relieves the user from the task of managing passwords with sites that are not directly compatible with the identity manager. The exposure of the associated solution to potential malware attacks depends first and foremost on what entity acts as a password manager, and if it is the phone, whether the password manager runs in a secure execution environment.

Users could also gain some increased security against site breaches. For instance, transaction tokens transmitted by the identity managers have no use if stolen. The output of a rolling code, for example, offers such benefits, as do cryptographic tokens based on digital signatures.

Exemplary Wearable Identity Authentication Usage Scenarios

In a first exemplary usage scenario, a user has a bracelet configuration of a wearable identity manager device, as described above, and two phones—one that she mostly uses for work, and another one she mostly uses for personal business. Both phones have software installed that is used for the authentication process: The work phone has a master data management (MDM) application installed by the user's employer, and the home personal phone has a personal application downloaded by the user from an application store. Both the MDM application and the personal application have been configured by downloading an encrypted user profile file associated with the user, and by registering a credential used for the association process between the phone and the bracelet. For the business phone, this credential is a biometric template associated with the fingerprint sensor on the business phone. For the personal phone, it is a password. Both of these credentials are stored in a secure manner (e.g., in a secure storage, or hashed and stored).

In a typical morning, the user will get up, shower, and then put on her bracelet. As she closes the clasp of the bracelet, the wearable identity manager of the bracelet is automatically put in the association stage. This will wake up her personal phone when the user gets within radio distance of the phone, which may be slightly less than one meter. The personal phone detects a low-power Bluetooth signal emitted by the wearable identity manager of the bracelet, and determines that this is for a unit that it has previously been Bluetooth paired with, creating a connection. After the Bluetooth connection has been established, the screen of the phone may display the message "connecting to Alice's bracelet", for example, soon followed by a text saying "Please enter the password for Alice's bracelet". The user then types her password into a small box on the screen of her personal phone. This is verified by the phone by hashing it and comparing the hashed password to the previously stored password associated with the association of the bracelet and the phone. The user then shakes the phone with the hand she is wearing the bracelet on. The accelerometer in the phone computes a signal digest from the accelerometer output and sends this to the bracelet—but only if the password the user previously entered was correct. The phone also transmits an indication that this is the user's password to the wearable identity manager of the bracelet. All this communication is secured using symmetric encryption associated with the Bluetooth connection. An accelerometer in the bracelet also generates a signal based on the motion, and the wearable identity manager of the bracelet compares the digest received from the phone with the generated signal, and if these correspond to each other, then the wearable identity manager accepts the association, storing that it is now worn by the user (which was conveyed to it by the phone.).

After breakfast, the user wants to log in to check her email on her personal phone. She starts the email application, which indicates that it needs an authentication (since the user has set it to be in locked mode when it is not used, requiring an authentication to access). Since the user is wearing her bracelet, she does not need to enter the PIN she otherwise would have to use to access her email. Instead, she gently shakes the phone using the hand with the bracelet. Her mail reader application uses the authentication library associated with, among other things, the wearable identity manager of the user's bracelet, which initiates a communication session with the wearable identity manager, which communicates over a secure channel to the phone that it is worn by the user. The authentication library unlocks the mail application, which allows the user to read her email.

Later, the user wants to access her bank account, and starts the banking application associated with her bank. The banking application runs on her personal phone, and also uses the authentication library described above. When it is started, it demands a login. The user then gently shakes her phone, and a session is started with the wearable identity manager of her bracelet. Similar to what is described above, the wearable identity manager transmits a signal to the personal phone, where it is processed by the code associated with the application library. The application library calls the application programming interface (API) of the password manager, indicating that the user is using the phone. The password manager determines the context of the call, which is an access to the user's bank, and looks up the user's user name and password from the secure repository used to store user names and credentials. These are input to the banking application, which upon receiving them conveys them over a secure sockets layer (SSL) session already started with the user's bank. The user's bank verifies that this is a correct login, and permits access to the account, communicating with the banking application on the user's personal phone.

Later, the user logs out, and then heads to the subway, on her way to work. Before leaving, she grabs her business phone. Instead of logging in to it to check her calendar, she gently shakes the business phone with the hand she is wearing the bracelet on. The business phone has also already been paired with the wearable identity manager, and starts a Bluetooth session with it. The association described above, between the user's personal phone and the wearable identity manager of the bracelet is not needed, since the bracelet has already been associated with the personal phone, and by doing that, been imprinted that it is worn by the user. The wearable identity manager conveys this fact to the business phone, which then automatically unlocks (no PIN needed).

The user looks at her schedule and realizes that she has time for a coffee before taking the subway. She goes to her neighborhood café, orders a coffee, and waves her hand to authenticate. Her bracelet establishes a Bluetooth connection with the point-of-sale computer, which verifies that the user has a stored financial, and automatically charges $3 on her credit card.

After purchasing her coffee, the user walks to the subway. As she goes through the turnstile, she does not need to wave her hand: to go through the turnstiles, you either need to have fed it a token or wear a registered bracelet. Here, it is assumed that the user has registered her bracelet. Before the turnstile allows the user through, it starts a connection with the user's bracelet, obtains an identifying value sent over an encrypted channel, where this value is associated with the user's account. Because her balance is more than the threshold for auto-refill (she set this to $10), no charge is needed on her credit card, and her balance is simply reduced by the amount of the subway fare.

Half an hour later, the user arrives at work. At her office, the turnstiles create a connection to the wearable identity manager in her bracelet, determines that she is a registered employee, and then let her in. When she sits down at her desk, her computer establishes a connection over WiFi to her work phone, which in turn establishes a connection to the wearable identity manager of her bracelet. The password manager in her phone is unlocked by the wearable identity manager after it compares the accelerator signal it receives from the phone with the signal generated by the built-in accelerometer. Of course, in addition to being essentially the same, they also have to indicate some movement—in this case, a brief shake. The password manager of the user's phone unlocks the user's computer, and she does not need to log in with password.

It should be noted that, in some of these uses of the wearable identity manager, a wave was required, and in others it was not. This is determined by the software making the connection to the wearable identity manager, and either an accelerometer signal is conveyed, or an indication that no wave is needed is conveyed. It is not possible for a rogue device to convey the wrong signal, since only paired devices are accepted by the wearable identity manager. It is also not possible for somebody wanting to access the user's bank account to wave their phones, since a similar waving action is not registered by her wearable identity manager. This way, the user does not have to enter any credentials all day. When she comes home, she takes of the bracelet, which is now automatically placing itself in a state that it needs to be associated with the user again before it will participate in any authentication. Therefore, a burglar who breaks in to the user's home while she steps out to see a friend is not able to use access her accounts—even though the burglar also steals one of the user's phones, since the burglar cannot authenticate as the user to successfully go through the association process.

In a second exemplary usage scenario, a user just purchased a watch configuration of a wearable identity manager device that detects when the wristband is opened or closed. As the user closes it for the first time, the wearable device manager places itself in a configuration state. The user downloads a companion application from the watch manufacturer's website, and installs this on his phone. When he starts the application, it requests for him to enter a name for the watch and select a password to associate his watch to his phone. (The user's phone does not have a biometric sensor.) After doing this, the wearable identity manager associated with the user's phone is associated with the information the user entered, and can be used to log in.

When the user visits an online auction site later that day, using his phone, the authentication library on his phone determines that he is logging in to a place that is not recorded in the password manager, and asks the user to wave his phone using the hand of the wrist he is wearing his phone on if he wants this user name and password stored in the password manager. The user likes this idea, and waves his hand. Next time he visits the auction site, he does not need to log in using his user name and password, as both of these will be auto-filled by the password manager of his phone and he will be logged in.

However, the user also logs in to various accounts using his laptop. He downloads a browser plugin to his laptop browser. The browser plugin asks the user to pair his phone to the laptop computer, which he does using a standard Bluetooth pairing protocol. It then requests permission to copy the repository associated with the password manager on the user's phone. The user does not give it this permission. The plugin then requests to use the password manager on the user's phone, which the user agrees to. As a result, the password manager on the user's phone is configured to pair with the user's laptop when needed.

When the user visits the auction site on his laptop, a routine on his laptop determines that this is a login session, and establishes a connection to the user's phone and the password manager on it. The password manager determines that it has a user name and credential stored for this domain, and initiates a connection with the wearable identity manager of the user's watch. The user gently shakes his hand, and the wearable identity manager determines that the signal it received from the phone matches the signal it generated itself, using the onboard accelerometer. As a result of this, and in a similar way as to what was described before, the password manager of the user's phone gets permission to use the password for the auction site on the laptop. As a result the user name and credential are conveyed to the laptop over a secure connection, or alternatively, are used to initiate a session to the auction site, where this session is then handed over to the laptop, and the user is logged in.

When the user later visits his bank website and logs in on his laptop, a routine in the browser plugin that the user installed determines that the user is logging in. It is displaying a request to add the user name and credential to the password repository on the user's phone. This is displayed on the screen of the user's computer. The user approves this request, and waves his phone to convey to the password manager on his phone that the user name and credentials that were sent to it from the user's laptop.

In this scenario, the previous user (hereinafter, "Alice") and the current user (hereinafter, "Bob) are friends, and Alice sometimes uses Bob's laptop. When she uses his laptop and visits a site or uses an application that requires a login, Bob's laptop will determine what phones are present that it is associated with. When Alice visits an auction site that both she and Bob use, Bob's laptop determines that both Alice and Bob's phones are present, and sets up sessions with both to complete a login. Since Bob is not using the laptop, but Alice is, she picks up her phone when she sees the login screen on the computer. She gives it a shake with the hand of the wrist on which she is wearing the bracelet that is associated with her wearable identity manager, and therefore her phone gets a signal indicating that an authentication is completed, and it engages its password manager routine to log in Alice on Bob's laptop.

Bob is also friends with another user, Cindy, who sometimes uses Bob's phone. Bob's phone has a password manager that includes both Bob's profile and Cindy's profile. When Cindy accesses a resource using Bob's phone, or using a computer connected to Bob's phone, then the password manager on Bob's phone determines whether to select Bob's or Cindy's profile—and decides on Cindy's profile—after Bob's phone, which is paired with Cindy's watch—receives a confirming signal from Cindy's watch. This signal is produced by comparing the accelerometer signals generated on Bob's phone and Cindy's watch.

One day, Cindy gets really upset with Bob, and configures her watch not to approve signals from Bob's phone. She does this using her own phone, which has been paired with her watch and is the master device of the watch. Bob could not change the configuration on her watch even if he wanted to, since his phone is not the master of her watch, but only associated with it. The next day, Cindy changes her mind and re-configures her watch to again allow sessions with Bob's phone. However, Bob has also reconfigured his phone to purge her profiles from the repository associated with his password manager, so Cindy cannot use his phone to perform authentications. She asks him to add her profiles again, and he agrees. He authenticates to his phone with a wave of his hand, using the wearable identity manager in his watch, and then approves Cindy to add her profile. She downloads her encrypted profile from a cloud storage she uses and adds it. The cloud storage knows that it is Cindy who is requesting the download, since it receives a request from Bob's phone, containing an encrypted request originating from Cindy's watch, and communicated to Bob's watch after the user approved Cindy to add her profile. She takes the phone in her hand, waves it, and the encrypted request along with the information of the cloud storage location is received and used by the password manager on Bob's phone. Cindy can now again use Bob's phone.

When Cindy buys a tablet computer a few weeks after, she pairs it with her watch and authorizes, using a wave, the password manager of her new tablet to download an encrypted copy of her profile from the cloud storage, similar to how this was done for Bob's phone. The encryption, in both of these cases, blocks an eavesdropper from learning the data, and uses a technology such as SSL.

In a third exemplary usage scenario, Dave has a watch that has similar functionality as the bracelets and watches described before, except that it does not have an accelerometer. Instead it has a button that Dave can press if he agrees with a request. When Dave pairs his phone with the watch, both the phone and the watch display a number on their screen, and Dave compares these to make sure that they correspond to each other. Since they do, he presses the button to approve, and they become associated with each other.

Later, when Dave takes off his phone, the phone reverts to a state when it again needs to be associated. Dave does the pairing again, and it is once again associated with the phone. He then wants to log in to a site using his phone, which sends a request to Dave's phone. A message is displayed on Dave's phone, asking him to approve the login request by pressing the button, or simply wait for three seconds without pressing the button if he does not want to approve the request. Dave presses the button, and his watch sends a signal to the phone, which when conveyed to the password manager initiates the lookup of the appropriate user name and credentials, followed by the logging in of Dave to the site.

Later, Dave is given a necklace with a wearable identity manager. This has an accelerometer, just like Dave's phone. To pair them, Dave simply puts on the necklace and walks with the phone in his hand—the phone he is using to associate the necklace with him. The necklace associates itself with the phone in the same way as Alice's bracelet associated itself with her phone, except that Dave does not wave it, but simply walks with the phone in his hand. The accelerometer output of the phone and of the necklace are compared, and a determination is made that they correspond to each other, after which the necklace is associated with Dave. Later, Dave wants to perform a purchase using his necklace as a source of identity. He presses the "approve purchase" button on his phone's screen and takes a few small steps or gently swings back and forth, allowing the wearable identity manager and the password manager to verify that it is used by the same person who pressed the "approve purchase" button.

In the case of Dave's necklace, this comparison is performed in his phone, as the necklace has an extra small battery that is only used to store the identity information of the wearer and detect when the necklace is taken off, so that the necklace can be put in the state where it once again needs to be associated with an account in order to perform an authentication. The radio transmitter of the necklace is powered by background radio signals, both for receiving and transmitting signals, just like a radio frequency identification (RFID) token.

After wearing it for a while, Dave lends the necklace to Alice, who associates it with her phone and uses it instead of her bracelet. When Alice returns it to Dave, the necklace associates itself to Dave and his phone as he puts it on.

In a fourth exemplary usage scenario, the aspects disclosed herein are implemented to replace the traditional log-in process. On a mobile device, such as a phone, the user may initiate the log-in process by simply waking the phone up (e.g., by picking it up, touching its screen, or pressing a button). The process may also be initiated by the user starting an application or attempting to access a resource referenced by an application. Example resources are user address books; emails; usage log files (such as the list of most recently placed phone calls); photos or directories of photos; and the ability to place toll calls. A desktop or laptop may be accessed in a similar way, where a mouse, mouse pad, or keyboard takes on the role of collecting data to be used to obtain assurance or confirmation.

Different resources may also be associated with different security levels—for example, a user may require an intermediate security level to unlock a phone; a low security level to access its email reader (once it is woken up); but a high security level to gain access to usage logs. The same user may then require a high security level to log in to his work computer, but only an intermediate security level to log in to his home computer, since this is only accessible by a small group of people in the first place. The user or his employer may also assign different levels of security to different types of access.

A special log-in case is also contemplated where either the identity manager or an associated proxy acts as a password manager for sites that are not compatible with the identity manager technology. Here, the log-in session may be moderated by one of these devices without exposing session secrets to the facilitating device.

In a fifth exemplary usage scenario, the aspects disclosed herein are implemented to facilitate payments, whether online or point of sale payments. To perform an online payment, the user may initiate the payment process by clicking a checkout button. For low and medium risk purchases, this may be sufficient, as it provides an intermediate level of security. However, for high-risk purchases, an explicit confirmation may be required instead. Here, many factors may influence the risk level of a transaction, such as the value; the type of merchandise; the user's history of purchases; and the location where the purchase is initiated. The level of security required may be selected by the user, the merchant, _financial institution, or a combination of these. For example, the user may set his/her preferences for minimum level of security, but these can be selectively increased by the policy set by the merchant or _financial institution. For a point of sale transaction, an explicit confirmation can be obtained as the user signs his/her signature on a point of sale terminal and the movement is correlated with the movement of his identity manager. This not only provides guarantees of user intent (which may be useful for disputed transactions) but may also help identify which one out of several possible users is to be associated with the transaction. Other types of payments—such as payments of subway fares—may not require more security than a proximity verification.

In a sixth exemplary usage scenario, the aspects disclosed herein are implemented for attribution purposes. To this end, it is noted that, by comparing accelerometer traces associated with a touch screen with accelerometer traces of bracelets, one can attribute user interactions on the screen even when multiple users touch the screen simultaneously, which may give rise to new types of gaming environments. This may also be one of the few usage scenarios where it makes sense for users to wear two bracelets at the same time. In the context of gaming, it may not be necessary to attribute actions to a user identity, but some form of pseudo-anonymity may be more practical.

Exemplary Networked and Distributed Environments

One of ordinary skill in the art can appreciate that various implementations for utilizing a computing device and related aspects described herein can be implemented in connection with any computer or other client or server device, which can be deployed as part of a computer network or in a distributed computing environment, and can be connected to any kind of data store. Moreover, one of ordinary skill in the art will appreciate that such aspects can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Figure 18:
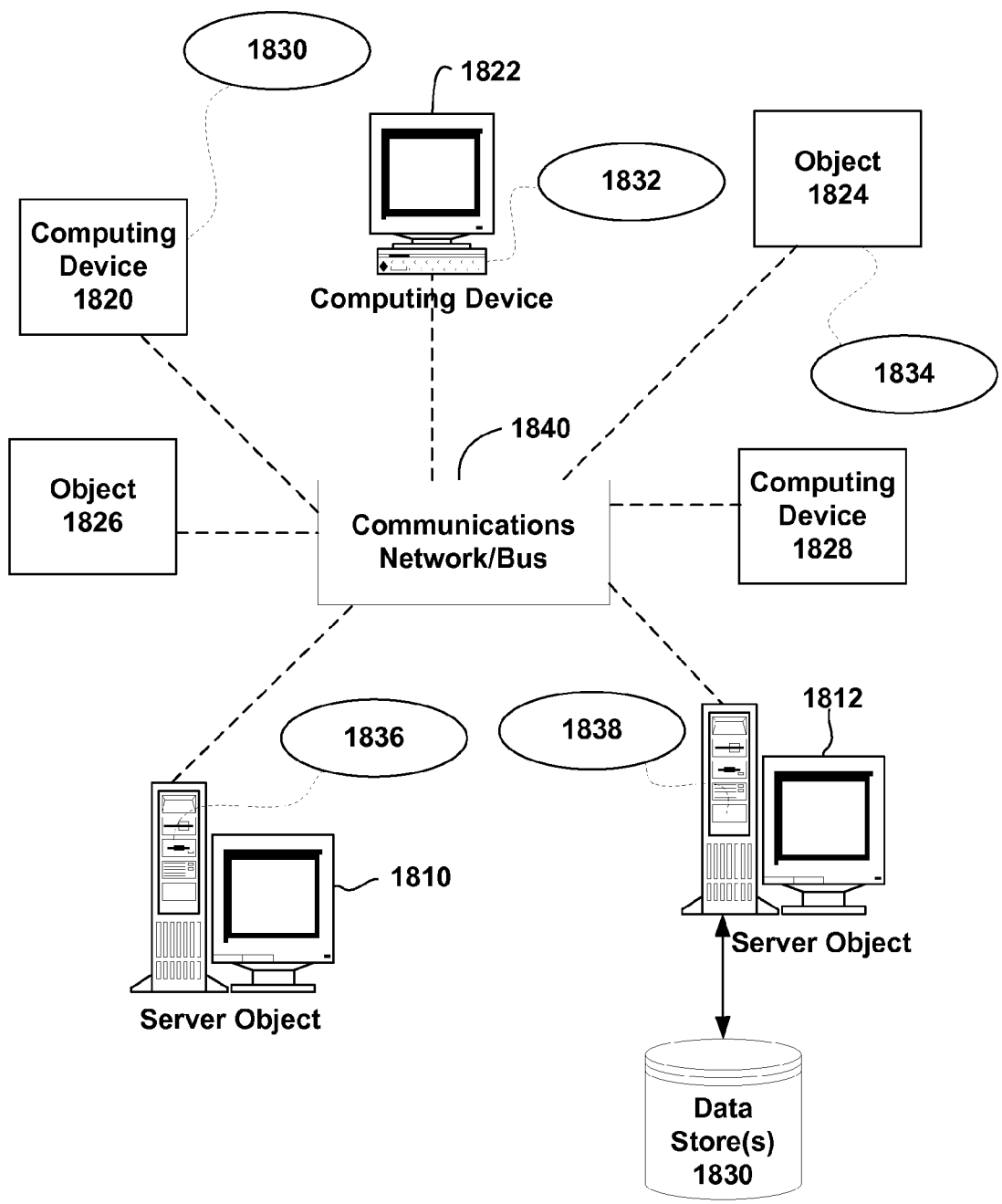
FIG. 18 is a block diagram representing exemplary non-limiting networked environments in which various embodiments described herein can be implemented.

FIG. 18 provides a non-limiting schematic diagram of an exemplary networked or distributed computing environment. The distributed computing environment comprises computing objects or devices 1810, 1812, etc. and computing objects or devices 1820, 1822, 1824, 1826, 1828, etc., which may include programs, methods, data stores, programmable logic, etc., as represented by applications 1830, 1832, 1834, 1836, 1838. It can be appreciated that computing objects or devices 1810, 1812, etc. and computing objects or devices 1820, 1822, 1824, 1826, 1828, etc. may comprise different devices, such as PDAs (personal digital assistants), audio/video devices, mobile phones, MP3 players, laptops, etc.

Each computing object or device 1810, 1812, etc. and computing objects or devices 1820, 1822, 1824, 1826, 1828, etc. can communicate with one or more other computing objects or devices 1810, 1812, etc. and computing objects or devices 1820, 1822, 1824, 1826, 1828, etc. by way of the communications network 1840, either directly or indirectly. Even though illustrated as a single element in FIG. 18, network 1840 may comprise other computing objects and computing devices that provide services to the system of FIG. 18, and/or may represent multiple interconnected networks, which are not shown. Each computing object or device 1810, 1812, etc. or 1820, 1822, 1824, 1826, 1828, etc. can also contain an application, such as applications 1830, 1832, 1834, 1836, 1838, that might make use of an API (application programming interface), or other object, software, firmware and/or hardware, suitable for communication with or implementation of the disclosed aspects in accordance with various implementations.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various implementations.

Thus, a host of network topologies and network infrastructures, such as client/server, peer-to-peer, or hybrid architectures, can be utilized. In a client/server architecture, particularly a networked system, a client is usually a computer that accesses shared network resources provided by another computer, e.g., a server. In the illustration of FIG. 18, as a non-limiting example, computing objects or devices 1820, 1822, 1824, 1826, 1828, etc. can be thought of as clients and computing objects or devices 1810, 1812, etc. can be thought of as servers where computing objects or devices 1810, 1812, etc. provide data services, such as receiving data from computing objects or devices 1820, 1822, 1824, 1826, 1828, etc., storing of data, processing of data, transmitting data to computing objects or devices 1820, 1822, 1824, 1826, 1828, etc., although any computer can be considered a client, a server, or both, depending on the circumstances. Any of these computing devices may be processing data, or requesting services or tasks that may implicate aspects and related techniques as described herein for one or more implementations.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the user profiling can be provided standalone, or distributed across multiple computing devices or objects.

In a network environment in which the communications network/bus 1840 is the Internet, for example, the computing objects or devices 1810, 1812, etc. can be Web servers with which the computing objects or devices 1820, 1822, 1824, 1826, 1828, etc. communicate via any of a number of known protocols, such as HTTP. As mentioned, computing objects or devices 1810, 1812, etc. may also serve as computing objects or devices 1820, 1822, 1824, 1826, 1828, etc., or vice versa, as may be characteristic of a distributed computing environment.

Exemplary Computing Device

As mentioned, several of the aforementioned implementations apply to any device wherein it may be desirable to include a computing device to facilitate implementing the aspects disclosed herein. It is understood, therefore, that handheld, portable and other computing devices and computing objects of all kinds are contemplated for use in connection with the various implementations described herein. Accordingly, the below general purpose remote computer described below in FIG. 19 is but one example, and the implementations of the subject disclosure may be implemented with any client having network/bus interoperability and interaction.

Although not required, any of the implementations can partly be implemented via an operating system, for use by a developer of services for a device or object, and/or included within application software that operates in connection with the operable component(s). Software may be described in the general context of computer executable instructions, such as program modules, being executed by one or more computers, such as client workstations, servers or other devices. Those skilled in the art will appreciate that network interactions may be practiced with a variety of computer system configurations and protocols.

Figure 19:
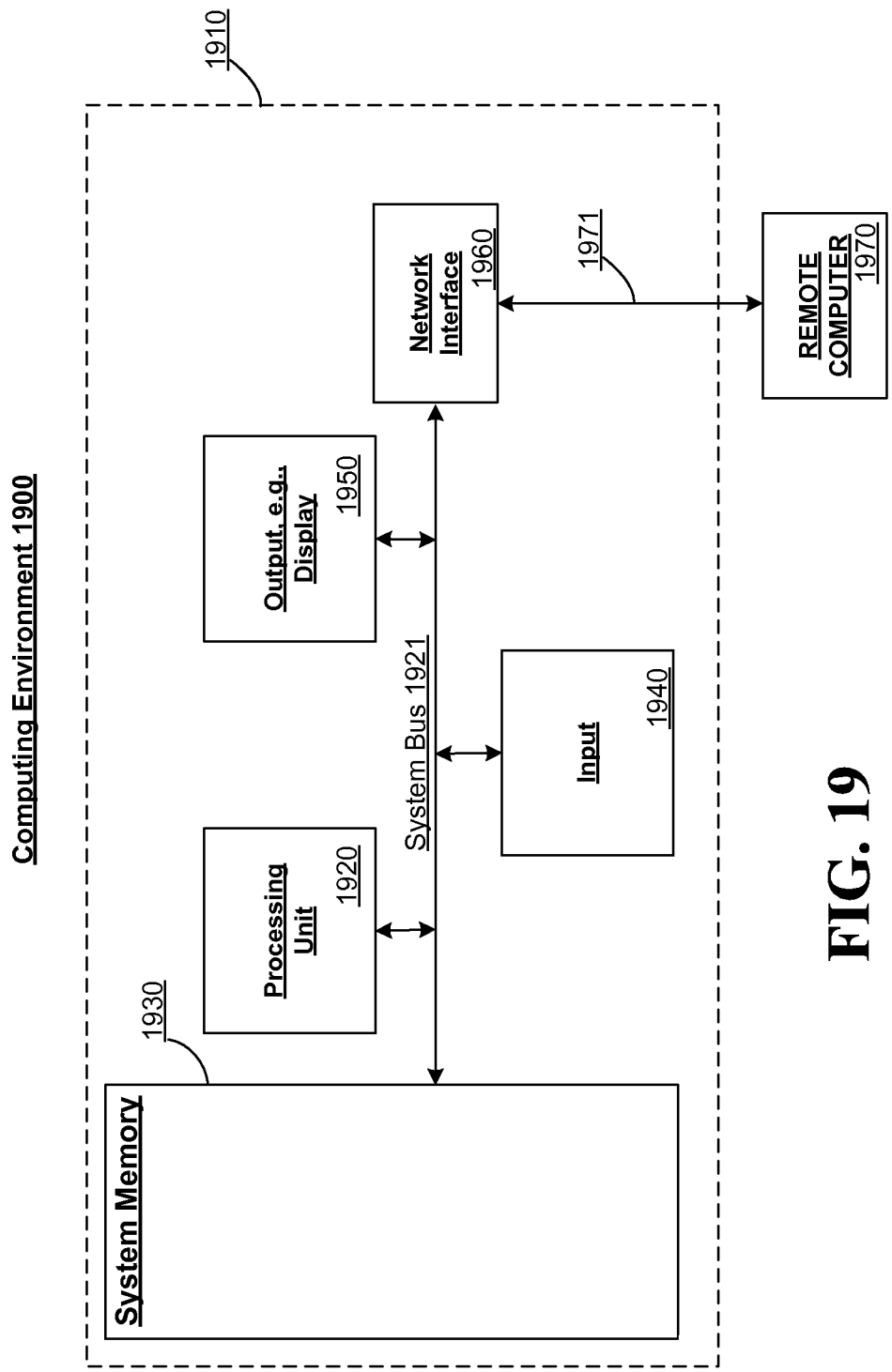
FIG. 19 is a block diagram representing an exemplary non-limiting computing system or operating environment in which one or more aspects of various embodiments described herein can be implemented.

FIG. 19 thus illustrates an example of a suitable computing system environment 1900 in which one or more of the implementations may be implemented, although as made clear above, the computing system environment 1900 is only one example of a suitable computing environment and is not intended to suggest any limitation as to the scope of use or functionality of any of the implementations. The computing environment 1900 is not to be interpreted as having any dependency or requirement relating to any one or combination of components illustrated in the exemplary operating environment 1900.

With reference to FIG. 19, an exemplary remote device for implementing one or more implementations herein can include a general purpose computing device in the form of a handheld computer 1910. Components of handheld computer 1910 may include, but are not limited to, a processing unit 1920, a system memory 1930, and a system bus 1921 that couples various system components including the system memory to the processing unit 1920.

Computer 1910 typically includes a variety of computer readable media and can be any available media that can be accessed by computer 1910. The system memory 1930 may include computer storage media in the form of volatile and/or nonvolatile memory such as read only memory (ROM) and/or random access memory (RAM). By way of example, and not limitation, memory 1930 may also include an operating system, application programs, other program modules, and program data.

A user may enter commands and information into the computer 1910 through input devices 1940 A monitor or other type of display device is also connected to the system bus 1921 via an interface, such as output interface 1950. In addition to a monitor, computers may also include other peripheral output devices such as speakers and a printer, which may be connected through output interface 1950.

The computer 1910 may operate in a networked or distributed environment using logical connections to one or more other remote computers, such as remote computer 1970. The remote computer 1970 may be a personal computer, a server, a router, a network PC, a peer device or other common network node, or any other remote media consumption or transmission device, and may include any or all of the elements described above relative to the computer 1910. The logical connections depicted in FIG. 19 include a network interface 1960 coupled to a network 1971, such as a local area network (LAN) or a wide area network (WAN), but may also include other networks/buses. Such networking environments are commonplace in homes, offices, enterprise-wide computer networks, intranets and the Internet.

As mentioned above, while exemplary implementations have been described in connection with various computing devices, networks and advertising architectures, the underlying concepts may be applied to any network system and any computing device or system in which it is desirable to implement the aspects disclosed herein.

There are multiple ways of implementing one or more of the aspects described herein, e.g., an appropriate API, tool kit, driver code, operating system, control, standalone or downloadable software object, etc. which enables applications to implement the aspects disclosed herein. Embodiments may be contemplated from the standpoint of an API (or other software object), as well as from a software or hardware object that facilitates implementing the aspects disclosed herein in accordance with one or more of the described implementations. Various implementations described herein may have aspects that are wholly in hardware, partly in hardware and partly in software, as well as in software.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In view of the exemplary systems described supra, methodologies that may be implemented in accordance with the disclosed subject matter can be appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

While in some implementations, a client side perspective is illustrated, it is to be understood for the avoidance of doubt that a corresponding server perspective exists, or vice versa. Similarly, where a method is practiced, a corresponding device can be provided having storage and at least one processor configured to practice that method via one or more components.

While the various implementations have been described in connection with the preferred implementations of the various figures, it is to be understood that other similar implementations may be used or modifications and additions may be made to the described implementation for performing the same function without deviating there from. Still further, one or more aspects of the above described implementations may be implemented in or across a plurality of processing chips or devices, and storage may similarly be affected across a plurality of devices. Therefore, the present invention should not be limited to any single implementation.

The invention claimed is:

1. A wearable identity manager device, comprising:
    a memory; and
    a processor communicatively coupled to the memory, the processor configured to:
        determine an association status between a user and the wearable identity manager device based in part on whether the wearable identity manager device is worn;
        pair the wearable identity manager device with a pairing device, wherein the pairing device is configured as a relay device between the wearable identity manager device and an external device based on whether the wearable identity manager device is continuously worn, and wherein the wearable identity manager device is configured to unpair from the pairing device in response to a discontinuity of the wearable identity manager device being worn; and
        transmit authentication data from the wearable identity manager device to the external device via the pairing device based on whether the wearable identity manager device is worn, wherein the authentication data is data used to determine a user authentication.

2. The wearable identity manager device of claim 1, the processor further configured to:
    monitor and collect motion data associated with a movement of the wearable identity manager device, wherein the authentication data includes the collected motion data, and wherein the collected motion data is configured to facilitate a pairing of the wearable identity manager device with the pairing device.

3. The wearable identity manager device of claim 2, wherein the motion data comprises a path traversed by the wearable identity manager device.

4. The wearable identity manager device of claim 1, wherein the processor is configured to associate the wearable identity manager device with the user via an association procedure, wherein the association status is based on an outcome of the association procedure.

5. The wearable identity manager device of claim 1, wherein the processor is further configured to retrieve sensor data from at least one of a gyro, a global positioning system (GPS) device, a touch-sensitive sensor, or a microphone, and wherein the authentication data further comprises the sensor data.

6. The wearable identity manager device of claim 1, wherein the processor is further configured to infer whether the wearable identity manager device is worn based on data retrieved from at least one of a clasp sensor, a pressure sensor, a temperature sensor, a pulse sensor, a motion sensor, or a stretch sensor.

7. The wearable identity manager device of claim 1, wherein the processor is further configured to:
    receive an authentication request;
    provide a credential; and
    transmit the credential based on the authentication request.

8. The wearable identity manager device of claim 1, wherein the processor is further configured to
    receive an authentication request;
    ascertain a security level associated with the authentication request; and
    transmit the authentication data based on the security level.

9. A non-transitory machine-readable storage medium having one or more instructions stored thereon, which when executed by at least one processor causes the at least one processor to:
    ascertain an association status between a user and a wearable identity manager device, wherein the association status is ascertained based in part on whether the wearable identity manager device is worn;
    pair the wearable identity manager device with a pairing device, wherein the pairing device is configured as a relay device between the wearable identity manager device and an external device based on whether the wearable identity manager device is continuously worn, and wherein the wearable identity manager device is configured to unpair from the pairing device in response to a discontinuity of the wearable identity manager device being worn; and
    transmit authentication data from the wearable identity manager device to the external device via the pairing device based on whether the wearable identity manager device is worn, wherein the authentication data is data used to determine a user authentication.

10. The non-transitory machine-readable storage medium of claim 9, the one or more instructions further comprising instructions to cause the at least one processor to:
monitor and collect motion data associated with a movement of the wearable identity manager device, wherein the authentication data includes the collected motion data, and wherein the collected motion data is configured to facilitate a pairing of the wearable identity manager device with the pairing device.

11. The non-transitory machine-readable storage medium of claim 9, the one or more instructions further comprising instructions to cause the at least one processor to associate the wearable identity manager device with the user via an association procedure, wherein the association status is based on an outcome of the association procedure.

12. The non-transitory machine-readable storage medium of claim 11, wherein the association procedure comprises matching a locally stored password with a password received from an associating device.

13. The non-transitory machine-readable storage medium of claim 11, wherein the association procedure comprises matching an associating movement of the wearable identity manager device with received data corresponding to a movement of an associating device.

14. The non-transitory machine-readable storage medium of claim 9, the one or more instructions further comprising instructions to cause the at least one processor to:
receive an authentication request; and
provide a credential based on at least one of a user action or an execution context extrapolated from the authentication request.

15. The non-transitory machine-readable storage medium of claim 9, the one or more instructions further comprising instructions to cause the at least one processor to:
receive an authentication request;
ascertain a security level associated with the authentication request; and
provide the authentication data based on the security level.

16. The non-transitory machine-readable storage medium of claim 15, wherein the security level is ascertained according to at least one of a user preference setting, an execution context, or one or more historical execution contexts.

17. A method to facilitate a wireless communication, comprising:
determining an association status between a user and a wearable identity manager device, wherein the determining comprises determining whether the wearable identity manager device is worn;
pairing the wearable identity manager device with a pairing device, wherein the pairing device is configured as a relay device between the wearable identity manager device and an external device based on whether the wearable identity manager device is continuously worn, and wherein the wearable identity manager device is configured to unpair from the pairing device in response to a discontinuity of the wearable identity manager device being worn; and
transmitting authentication data from the wearable identity manager device to the external device via the pairing device based on whether the wearable identity manager device is worn, wherein the authentication data is data used to determine a user authentication.

18. The method of claim 17, further comprising monitoring motion data associated with a movement of the wearable identity manager device, wherein the authentication data includes the motion data, and wherein the motion data is configured to facilitate a pairing of the wearable identity manager device with the pairing device.

19. The method of claim 17, further comprising associating the wearable identity manager device with the user via an association procedure, wherein the association status is based on an outcome of the association procedure.

20. The method of claim 19, wherein the association procedure comprises matching a locally stored password with a password received from an associating device.

21. The method of claim 19, wherein the association procedure comprises matching an associating movement of the wearable identity manager device with received data corresponding to a movement of an associating device.

22. The method of claim 17, further comprising:
storing a credential associated with the user; and
providing the credential to the pairing device in response to an authentication request.

23. The method of claim 22, further comprising:
ascertaining a security level associated with the authentication request; and
limiting an amount of the credential transmitted to the pairing device based on the security level.

24. A wearable identity manager device, comprising:
means for determining an association status between a user and the wearable identity manager device, wherein the association status is based in part on whether the wearable identity manager device is worn;
means for pairing the wearable identity manager device with a pairing device, wherein the pairing device is configured as a relay device between the wearable identity manager device and an external device based on whether the wearable identity manager device is continuously worn, and wherein the wearable identity manager device is configured to unpair from the pairing device in response to a discontinuity of the wearable identity manager device being worn; and
means for transmitting authentication data from the wearable identity manager device to the external device via the pairing device based on whether the wearable identity manager device is worn, wherein the authentication data is data used to determine a user authentication.

25. The wearable identity manager device of claim 24, further comprising means for monitoring motion data associated with a movement of the wearable identity manager device, wherein the authentication data includes the motion data, and wherein the motion data is configured to facilitate a pairing of the wearable identity manager device with the pairing device.

26. The wearable identity manager device of claim 25, wherein the motion data comprises a path traversed by the wearable identity manager device.

27. The wearable identity manager device of claim 25, wherein the means for monitoring further comprises means for retrieving sensor data from at least one of a gyro, a touch-sensitive sensor, or a microphone, and wherein the authentication data further comprises the sensor data.

28. The wearable identity manager device of claim 24, wherein the means for determining further comprises means for inferring whether the wearable identity manager device is worn based on data retrieved from at least one of a clasp sensor, a pressure sensor, a temperature sensor, or a stretch sensor.

29. The wearable identity manager device of claim 24, further comprising:
means for receiving an authentication request; and means for ascertaining a security level associated with the authentication request, wherein the means for transmitting comprises means for transmitting the authentication data to the pairing device based on the security level.

30. The wearable identity manager device of claim 29, wherein the means for ascertaining comprises means for selecting the security level from a plurality of possible security levels.

* * * * *